United States Patent
Horton et al.

(10) Patent No.: US 9,622,779 B2
(45) Date of Patent: Apr. 18, 2017

(54) METHOD AND DEVICES FOR A SUB-SPLENIUS / SUPRA-LEVATOR SCAPULAE SURGICAL ACCESS TECHNIQUE

(71) Applicants: William C Horton, Duxbury, MA (US); John Riley Hawkins, Cumberland, RI (US); Christopher L Ramsay, West Wareham, MA (US); Edward Zalenski, Lakeville, MA (US); Alexander Grinberg, Newton, MA (US); Hassan Serhan, South Easton, MA (US); Ernest Quintanilha, Norton, MA (US)

(72) Inventors: William C Horton, Duxbury, MA (US); John Riley Hawkins, Cumberland, RI (US); Christopher L Ramsay, West Wareham, MA (US); Edward Zalenski, Lakeville, MA (US); Alexander Grinberg, Newton, MA (US); Hassan Serhan, South Easton, MA (US); Ernest Quintanilha, Norton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 588 days.

(21) Appl. No.: 13/627,294

(22) Filed: Sep. 26, 2012

(65) Prior Publication Data
US 2013/0109925 A1    May 2, 2013

Related U.S. Application Data

(60) Provisional application No. 61/552,433, filed on Oct. 27, 2011, provisional application No. 61/663,074, filed on Jun. 22, 2012.

(51) Int. Cl.
*A61B 17/56* (2006.01)
*A61B 1/06* (2006.01)
(Continued)

(52) U.S. Cl.
CPC ............... *A61B 17/56* (2013.01); *A61B 1/06* (2013.01); *A61B 1/32* (2013.01); *A61B 17/0218* (2013.01);
(Continued)

(58) Field of Classification Search
None
See application file for complete search history.

(56) References Cited

U.S. PATENT DOCUMENTS

2004/0143167 A1* 7/2004 Branch et al. ............... 600/212
2005/0288677 A1* 12/2005 Stauber ........................ 606/90
(Continued)

FOREIGN PATENT DOCUMENTS

EP          2353537 A1    8/2011
WO    WO 2011/116379 A2    9/2011

OTHER PUBLICATIONS

Deepak Awasthi, MD. and H. Bruce Hamilton, MD. / "Posterolateral Approach to the Cervical Spine"/ 2004/ Louisiana State University Medical Center Dept. of Neurosurgery.*
(Continued)

*Primary Examiner* — Anu Ramana
*Assistant Examiner* — Jessica Weiss
(74) *Attorney, Agent, or Firm* — Raymond N. Scott, Jr.

(57) ABSTRACT

A novel posterolateral inter-muscular approach has been developed to access the cervical spine. The approach includes elevating the splenius capitis and trapezios muscles dorsally to create a window for deep spine access, wherein the window comprises
i) an anterior superior border of the trapezius muscle;
ii) an anterior inferior border of the splenius capitis muscle, and
(Continued)

iii) a posterior superior border of the levator scapulae muscle.

Preferably, a device such as an implant or an instrument is then passed through the window to manipulate the spine.

20 Claims, 23 Drawing Sheets

(51) Int. Cl.
    *A61B 1/32*     (2006.01)
    *A61B 17/02*     (2006.01)
    *A61B 17/06*     (2006.01)
    *A61B 90/30*     (2016.01)

(52) U.S. Cl.
    CPC ......... *A61B 17/06* (2013.01); *A61B 2090/309* (2016.02)

(56) References Cited

U.S. PATENT DOCUMENTS

2007/0010716 A1*   1/2007   Malandain et al. .......... 600/224
2009/0177241 A1*   7/2009   Bleich et al. ............... 606/86 R
2013/0012990 A1*   1/2013   McClellan .................... 606/232

OTHER PUBLICATIONS

Lance K. Mitsunaga, Eric O. Klineberg, and Munish C. Gupta/ "Laminoplasty Techniques for the Treatment of Multilevel Cervical Stenosis"/ 2011/ Dept. of Orthoaedic Surgery, Univ. of California Davis Medical Center.*

Preliminary Amendment Report on Patentability, International Application No. PCT/US2012/060754; mail date May 8, 2014.

* cited by examiner

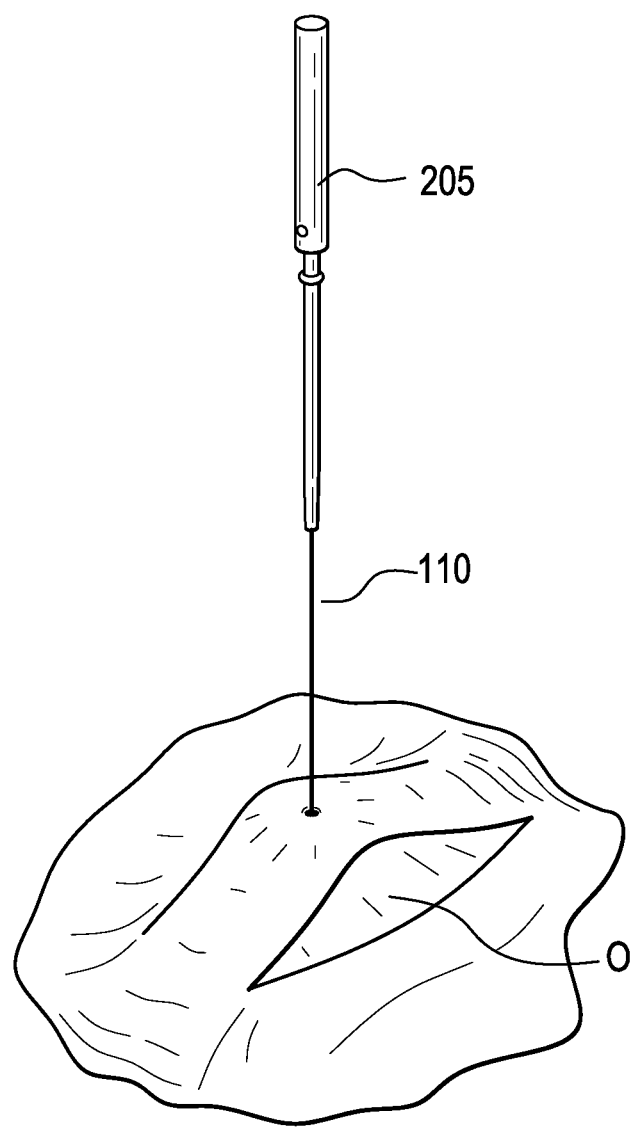

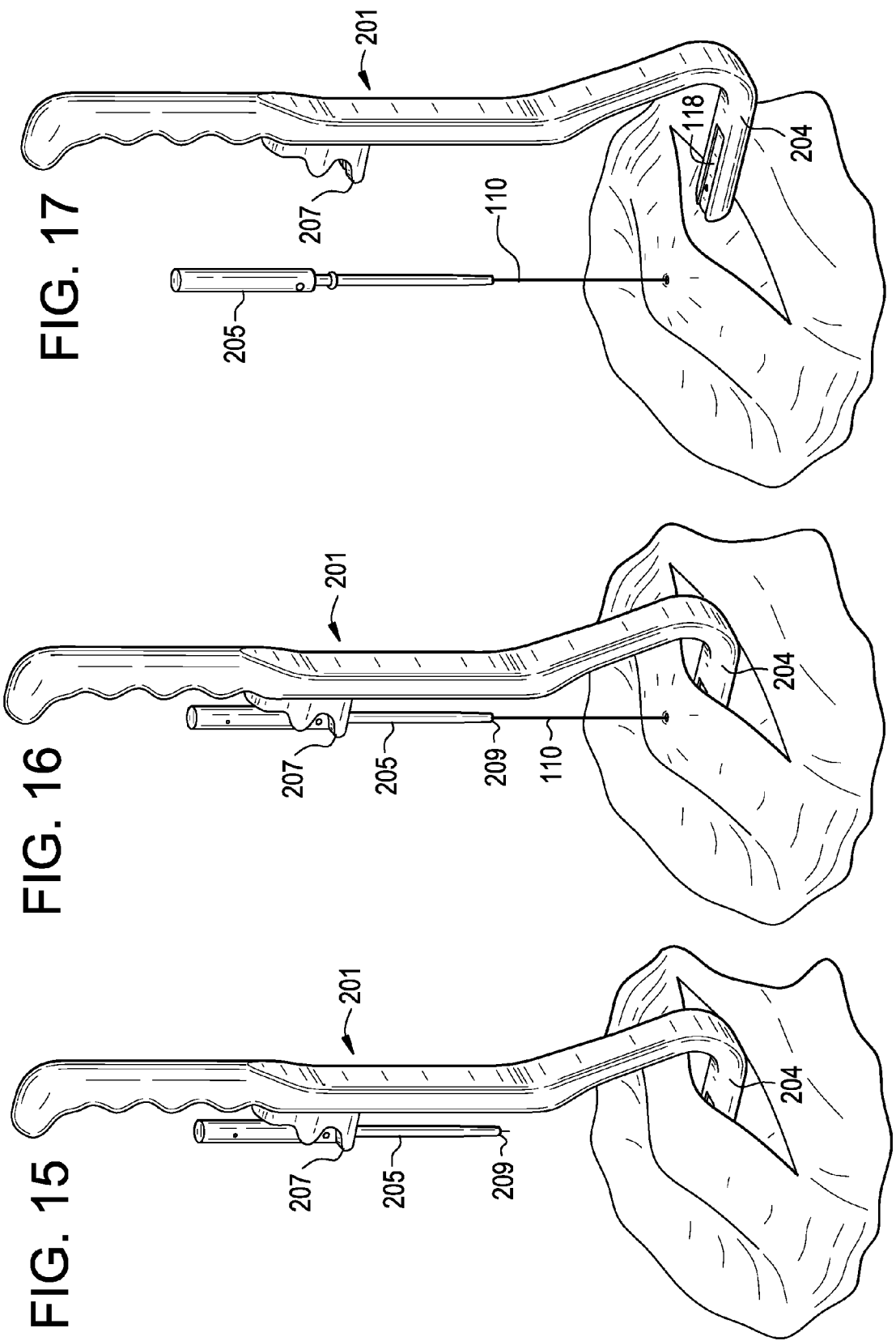

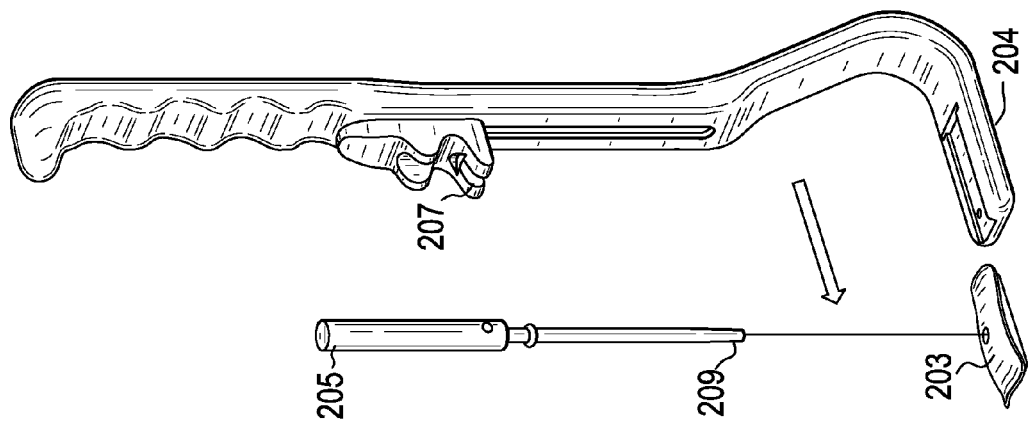
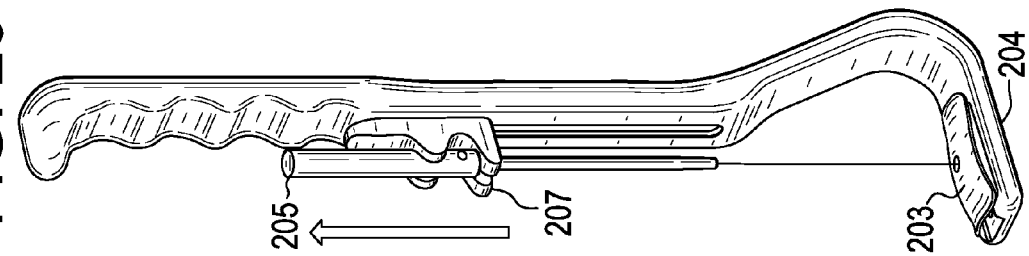
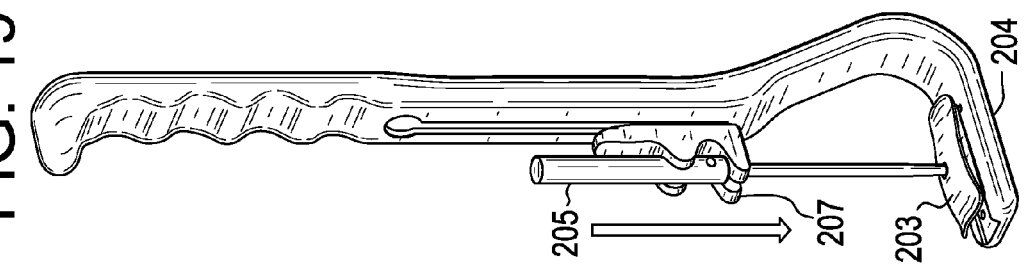
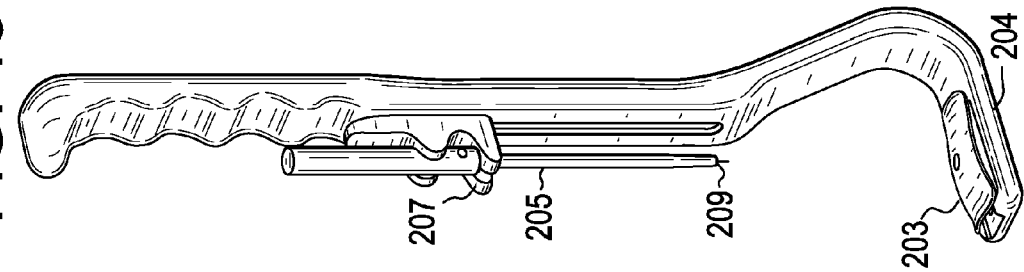

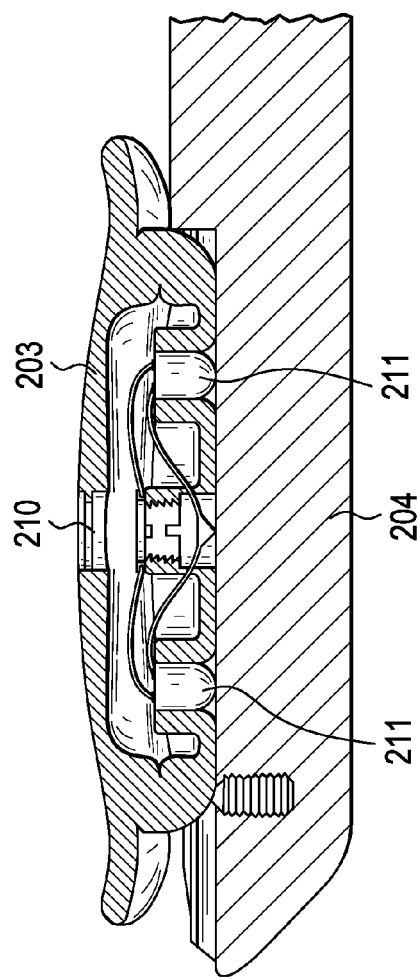
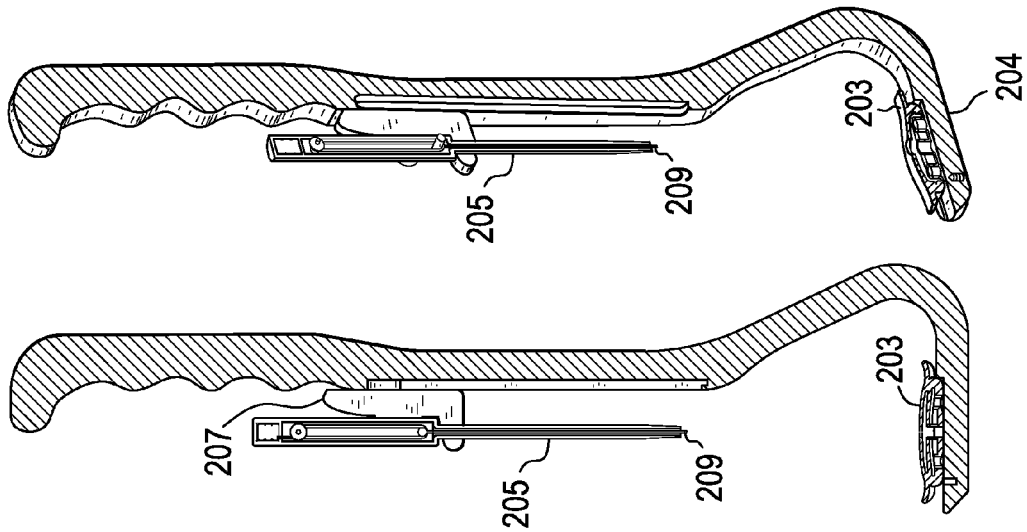

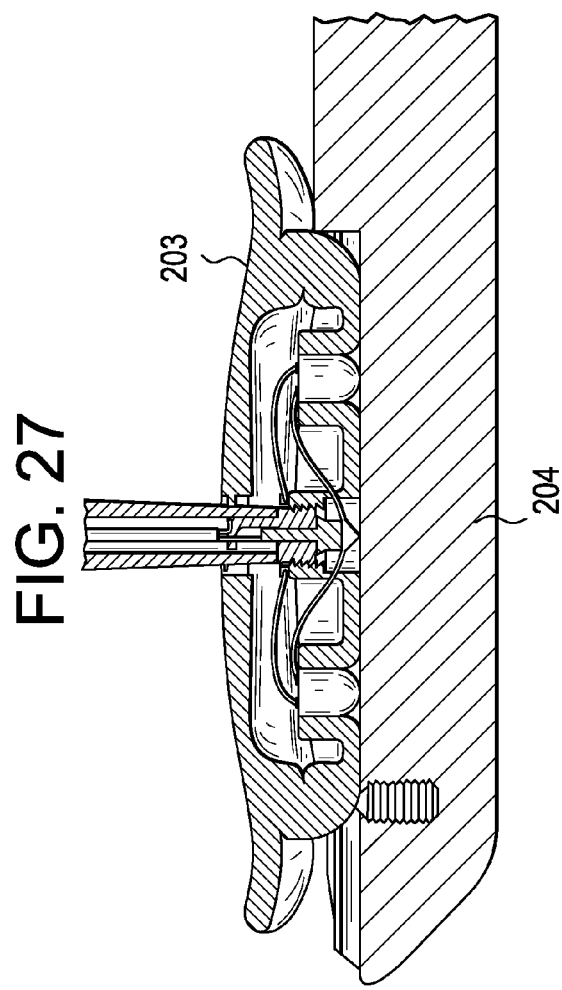
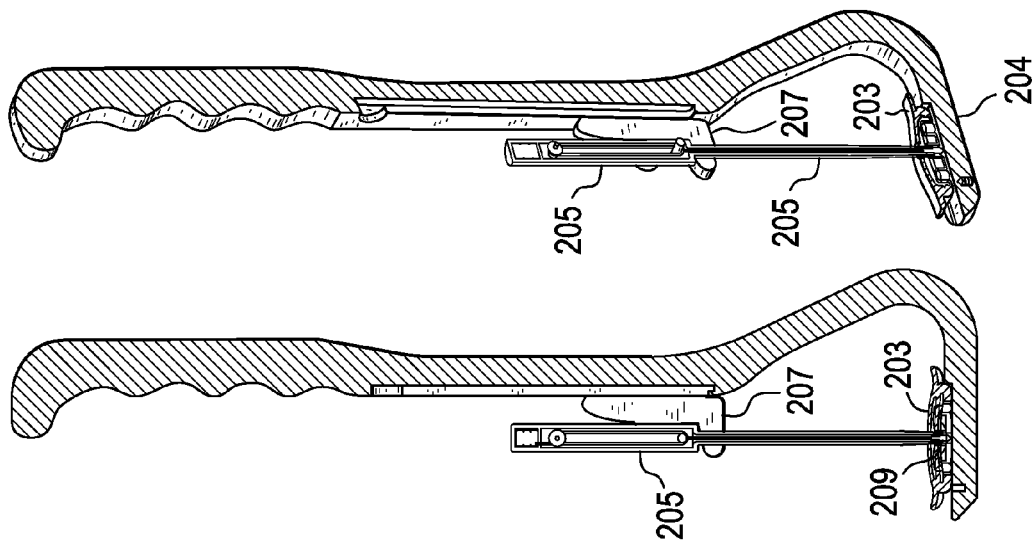

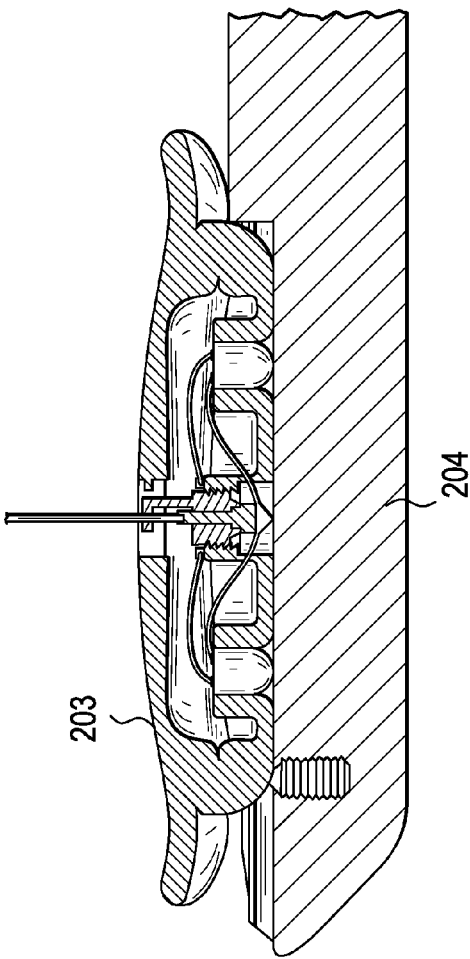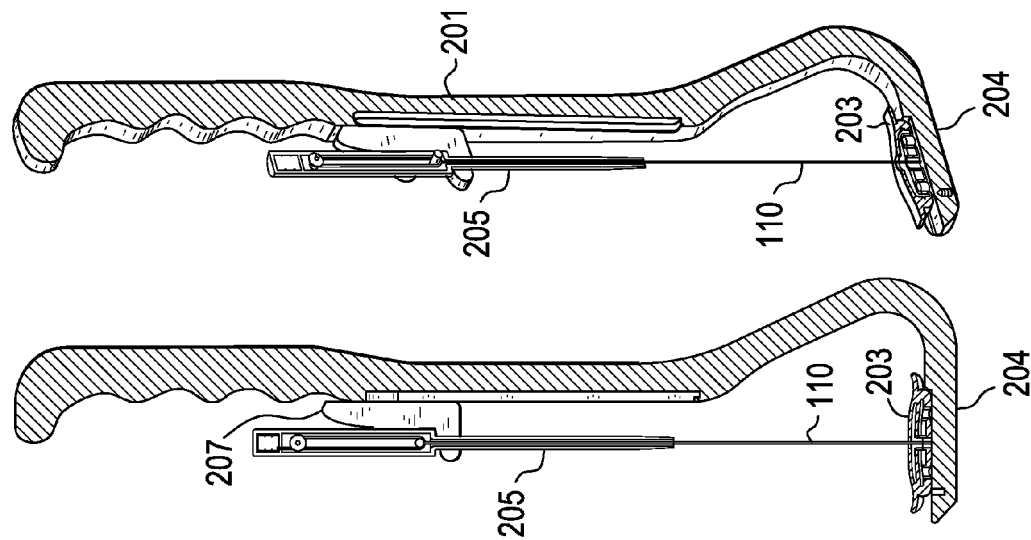

METHOD AND DEVICES FOR A SUB-SPLENIUS / SUPRA-LEVATOR SCAPULAE SURGICAL ACCESS TECHNIQUE

CONTINUING DATA

This application claims priority from U.S. Ser. No. 61/552,433, filed Oct. 27, 2011, entitled "Method and devices for a sub-splenius/super-levator scapulae surgical access technique", Horton et al., the specification of which is incorporated by reference in its entirety.

This application also claims priority from U.S. Ser. No. 61/663,074, filed Jun. 22, 2012, entitled "Method and devices for a sub-splenius/super-levator scapulae surgical access technique", Horton et al., the specification of which is incorporated by reference in its entirety.

BACKGROUND OF THE INVENTION

Surgical access for superficial structures such as the eye, skin or teeth present little challenge. However, for treatment of pathology deep in the body, the surgical approach may risk violating or potentially injuring several healthy tissues in the process of reaching the surgical target. In addition, an optimal surgical route would not place any vital structures at risk when at all possible. Because, however, the spinal column lies deep in the very center of the body, it presents unique challenges for surgical access to its pathologic targets. Posteriorly, spinal surgical access must traverse multiple anatomic planes and deep layers of muscle. Anteriorly and laterally, besides the muscular impacts, approaches also frequently engage multiple vital structures in the passage between the skin and the target. These anatomic realities by necessity create a major part of the overall risk and morbidity for the patient, as well as more technical challenges for the surgeon.

Pathology in the cervical spine is ubiquitous and commonly includes herniated disc, stenosis, disc degeneration, facet disease, tumor, trauma and other instabilities. The majority of cervical problems requiring surgery occur between $C_2$ and $T_1$, and currently there are two common surgical approaches for accessing this region—the anterior and the midline posterior approaches. See FIG. 10. While both are commonly utilized, each has significant drawbacks and unique morbidities that should ideally be overcome due to their common application.

1. Current Approaches: Description, Advantages and Problems

A. Anterior Approach

The patient is positioned supine and the surgical team is standing throughout the procedure. A three to four centimeter incision is placed either on the left or right medial boarder of the sternocleidomastoid, with the plane of dissection passing medial to the carotid sheath. Incisions are normally placed transversely and are extended slightly when access to more than two vertebral bodies is necessary. A vertical incision is usually utilized when more than 3 vertebral bodies need to be accessed simultaneously, with this incision being five or more centimeters in length. By necessity, the carotid sheath must be mobilized laterally and the esophagus, thyroid, trachea, and larynx are mobilized medially. This is mostly an inter-muscular plane of dissection with muscular damage being limited to the platysma and the omohyoid superficially, and the longus colli deep on the anterior aspect of the spine. Collectively, this amount of muscular disruption is typically considered relatively insignificant. However, there are several vital structures in the route of this dissection. Airway retraction and manipulation or post-op swelling can lead to post-op airway obstruction which can be fatal in rare cases. This has lead to many adjustments in retraction and ET cuff management but the potential still exists, particularly in prolonged cases. The carotid artery and internal jugular vein can be injured during the approach or plaques dislodged from the carotid in older patients potentially resulting in a stroke. Additionally, vocal changes postoperatively can occur due to significant retraction or scarring of the larynx or unintended injury to the laryngeal nerves, especially the recurrent, which is potentially in the plane of dissection. Furthermore, dysphagia is frequent after this approach from swelling, scarring and the required esophageal retraction. This dysphagia, often resolves over several months but can be extremely troublesome for daily function and can result in permanent difficulty with eating and even aspiration. Other important nerve structures at risk include the sympathetic trunk which lies on the anterior aspect of the longus colli (Horner's syndrome) and the hypoglossal nerve if the exposure is extended to C4 or above. The superior, middle and inferior thyroid arteries and veins are directly in the field of approach and must be controlled as well, representing one of the other potential causes of rare but life threatening post op airway obstruction from hematoma.

Once the spine is reached, the surgeon has excellent access to the disc. However, it becomes necessary to remove the entire anterior longitudinal ligament and the disk structure itself in order to reach the typical pathologies at the posterior aspect of the disc space, as well as gaining access to the spinal canal and the nerve roots in the foramen. Consequently, when decompressions of the spinal cord or nerve roots is required from an anterior approach, some type of motion segment reconstruction is usually mandated due to the subsequent lost of motion segment integrity that is required through this route. This means that virtually every standard anterior cervical approach results in some type of arthroplasty or fusion to reconstruct the loss of motion section integrity that may be entirely secondary to the approach (even if fusion was not indicated by the patient's original pathology). Anterior disc without fusion was done in the 1960s-70s but now have been abandoned. This is in sharp contrast to current treatment the lumbar spine where surgeons commonly perform posterior decompressive procedures without any fusion or reconstruction, since that anatomic route of approach does not create enough disruption to mandate some type of reconstruction as an aftermath. Besides increasing the need for fusion, the anterior cervical approach also presents another challenge in that if nerve compression is located laterally, the exposure will be limited by the uncovertebral joint, and more significantly, the vertebral artery. Injury to this vital structure can occur with dissection in the foraminal area or if reconstruction deviates off the midline. Vertebral artery injury can potentially be catastrophic.

The anterior cervical exposure usually requires self retaining retractors, which can occasionally injure the esophagus or the sympathetic trunk if they migrate out of position. For this reason an assistant is often required to stabilize retractors in their position, and assistance is also often necessary in accessing the contra lateral side of the exposure and in maintaining orientation to the midline during reconstruction. Typically this exposure can be extended up to $C_3$ and down to $C_7$ or $T_1$ depending on the position of the clavicle. Even with nasotracheal intubation, the mandible can occasionally obstruct clear access to the upper cervical area. When revision is required after the anterior cervical approach, access is often done on the contra-lateral side due to major challenges with scaring around all the vital structures on the side of prior approach, making revision on the ipsilateral repeat dissection potentially risky.

Only pathology in the anterior aspect of the spine and the anteromedial foraminal region can be visualized through this approach.

Primary advantages to this approach are universal surgeon familiarity, quick and easy dissection for the surgical team, very limited muscle damage, and minimal post operative surgical pain with quick return to function for the uncomplicated patient.

Primary problems associated with the approach include putting several vital structures at risk in the approach route, potential for rare but catastrophic complications, dysphasia, limited foraminal access, and almost always requires extensive reconstruction or fusion.

B. Posterior Midline Approach:

The patient is positioned prone with the surgical team standing throughout the procedure. The main difference versus the anterior approach is that there are virtually no vital structures at risk in this surgical route, but extensive muscle detachment, dissection, and disruption is mandatory. This approach utilizes a midline vertical incision and requires detachment of all three layers of cervical musculature. The superficial, intermediate, and deep layers are all detached and dissected from the tip of the spinous process down across the deep surface of the lamina to the lateral aspect of the lateral mass. This involves detachment of the longissimus, spinalis, trapezius, semi spinalis, splenius, multifidus, rotatores and rhomboid at C7. Because of the bulk and depth of these combined posterior cervical muscles, the dissection usually extends at least 1 level above and below the target level just to gain adequate access at the ends of the required field. This can create risk of damage to healthy motion segments. Although this is a "subperiostial" exposure, all of these muscles are detached, and exposure of the lateral mass usually disrupts the dorsal ramus at the dissected levels either directly or through the position of the deep retractors. Self retaining retractors (Cerebellar or other) are required, and these by necessity exert significant pressure on the muscle structures due to the depth and bulk of these posterior cervical muscles. This retractor pressure can result in ischemic necrosis of the muscle tissue bilaterally. Additionally, the midline ligamentous structures (ligamentum nuchae and the interspinous ligaments) are usually detached, which disrupts the integrity of the entire posterior musculo-ligamentous system in the cervical spine. Additionally, as these muscular structures span multiple segments, this cervical posterior exposure can potentially impact muscular and ligamentous function far beyond the extent of the approach, by injuring structures that span from the occiput to the upper thorasic region.

Once the deep cervical spine is exposed, the surgeon has good access to the dorsal elements and the spinal canal. Midline laminectomy or other dissection can be done as well as foraminal dissection. The limits of the thick muscular retraction laterally creates some restriction for far lateral exposure. The working angle that the surgeon has provides excellent opportunity for placing lateral mass instrumentation, but creates significant challenges for placing cervical pedicle screws where the converging angle of the instrumentation is at odds with the thick lateral musculature. Access to antero-lateral pathology such as herniated disc can be accomplished although there are limitations to what can be done on the floor of the spinal canal due to considerations of spinal cord safety. It is noteworthy that the structures best accessed through this approach are the spinous processes, while in fact virtually no significant pathologies are recognized in this midline area.

As is seen in the lumbar spine (and in contrast to the anterior cervical approach), posterior cervical access often does not require a fusion, and lends itself to decompressive laminectomy or forminotomy procedures without fusion or reconstruction when appropriate. This approach has also been expanded to include laminoplasty although post op muscular pain and stiffness has been a problem. Closure of this multi-muscular incision requires multiple deep layers and is sometimes challenging both cosmetically as well as in achieving excellent re-approximation of each anatomic level.

Problems associated with this approach include extensive deep muscular and ligamentus disruption, difficult bilateral retraction, significant often prolong post operative incisional pain, difficult convergence angle to pedicles and referred pain from injury of soft tissue structures.

Advantages of this approach include surgeon familiarity, no vital structures in the surgical route, no catastrophic potential approach complications and finally, it, does not demand fusion as an aftermath in many situations.

Approach-Related Prior Art

The literature suggests that there are substantial problems and potentially disproportionate problems related to the anterior approach. Although the anterior approach is quite commonly used, popular and widely accepted, there are obviously ongoing issues that need to be addressed. A survey of the activity in the literature would suggest that perhaps the posterior approach has either created less difficulties or at least garnered less attention with respect to potential complications. While recognizing that both approaches have important clinical utility, their deficiencies do suggest a need for improvement and perhaps indicate a rationale to look into the posterior surgical approach options that seem to have a better safety profile with less potential for catastrophy. There will always be some needs for both, as the surgical approach must "go where the pathology is" but we may be able to improve the safety profile of many cases.

While the typical posterior approach has been almost universally utilized via the midline, there have been exceptions that have allowed for creation of postero-lateral or lateral cervical approaches that will be outlined below, although none of them mimic in any way the procedure that we have described.

In 2009 B. Zhao, *Spinal Journal* 9:822-829 2009 described a posterolateral exposure for excision of extra foraminal tumors. However, this utilizes a traditional midline incision and a standard medial to lateral exposure out to the lateral mass, detaching all the muscles in a standard approach. Further extension of their dissection is then taken by detaching the Levator scapulae and the scalene muscles to provide access to the brachial plexus and anterior structures. Thus, the plane of dissection is exactly opposite to that which we are utilizing, and our approach intentionally spares the muscles they are detaching specifically for the purpose of protecting the brachial plexus. It would be theoretically possible, to convert our exposure to an extensile approach that would allow access to the brachial plexus and the lateral cervical spine or even anterior cervical structures. This extensile application would no longer be considered "inter-muscular" or in any way minimally invasive or tissue sparing, although it certainly may have utility in unusual pathologic circumstances.

S. J. Hyun Surgical *Neurology* 72:409-13, 2009 described another posterolateral approach which is based on the posterior aspect of the sternocleidomastoid. This surgical approach mobilizes the V-2 segment of the vertebral artery for access to the lateral cervical area and is particularly targeted to the very upper cervical spine. This approach does not engage in any way the plane of dissection on the posterolateral cervical spine as we have described, and remains anterior to the Scalenes.

Upper cervical and high cranio cervical posterior or far lateral approaches have been described for pathology involving the foramen magnum, clivus, and the C1-C4 region. Although these approaches do place the skin incision on the lateral cervical area, all of these techniques involved detachment of the splenius, semispinalis, and even the longissimus from the skull K. A. Tsutsumi et al Neurological Surgery 23:301-09 1995; X. G. Tong Chinese Journal of Contemporary Neurology and Neurosurgery 8:38-42 2008.). Therefore, all of these craniocervical and far posterolateral pre-cervical approaches are muscle detaching and radically different from our muscle sparing technique. Additionally, the posterolateral upper cervical approaches discussed above also involve lateral positioning of the patient, with the surgical team typically standing which are in sharp distinction to our technique. The plastic surgery literature includes descriptions of multiple flaps in the cervical area utilizing the superficial and intermediate layers for reconstruction. A splenius Capitis flap and others for reconstruction of pathologies such as Arnold-Chiari malformation have been described (Elshay etal N. I. Elshay Plastic and Reconstructive Surgery 9 3:1082-86 1994). These of course involve detachment and mobilization of muscular structures and are in no way an inter-muscular approach for cavity creation such as we have outlined. Tunneling techniques and pocket creating techniques have been widely utilized in plastic surgical strategies in the areas of the chest and the abdominal wall for various reconstructive applications although these have not been used with respect to surgery on the spinal structures themselves.

The importance of the superficial and intermediate cervical musculature that we are preserving by this new technique has been suggested in multiple areas of the literature. Panjabi et al estimated that 80% of stability of the cervical spine is muscular, with only 20% being osteoligamentous in nature (Clinical Biomechanics 1998). A 2011 study by E. Okada et al, EuroSpine Journal published online Mar. 23, 2011 Springer, with MRI evaluation showed a clear age dependent atrophy of the splenius and semispinalis which are the largest of the posterior muscles in the cervical spine. This was seen throughout all cervical levels, and highlights the critical importance of preserving as much of this muscle function as possible particularly in the middle-aged and older patients. All of the key cervical muscles described by M. S. Conley et al Spine 20: 2505-12 1995 for extension (semispinalis and splenius) and as well as for rotation (splenius, semispinalis, Levator scapuli and scalene) are all preserved by the approach that we have outlined.

A detailed anatomic study by A. Ono et al Spine 33:349-54 2008 demonstrated wide variations in anatomic insertion patterns of cervical musculature. This includes the splenius, serratus, and rhomboid. This work stresses the need to preserve tendinous attachments to the various and contiguous posterior midline structures, and emphasizes the unpredictable clinical impact of detaching these muscles from their midline insertions as is done in today's standard approaches. All of the Nuchal based musculature was felt to be critical to craniocervical function through the analysis of this study.

A. N. Vasavada et al Spine 23:412-22 1998 reported that the largest moment arms throughout the head and neck system are generated by the semi spinalis and splenius capitis in extension, and by the trapezius in axial rotation. This type of work further emphasizes the critical importance of preserving midline boney attachments of these superficial and intermediate muscular layers which is in sharp contrast to what is currently done with the standard posterior cervical exposures. The mechanical importance of the splenius muscle is further illustrated by treatments that have been described for splenius type torticollis. In such cases, approaches to the upper splenius and semispinalis have been described for the purpose of selective dennervation. This approach involves a midline based dissection with intentional sectioning of the motor branches, which is in sharp contrast to our approach which involves the approach plane from a lateral direction specifically preserving these motor branches as much as possible.

There is additional prior art with respect to elevating type retractor systems. These have been utilized primarily in the fields of plastic surgery and general surgery. The Laprolift system was described for access to the retro peritoneal space and the abdominal cavity. Its utilization was extended to be an adjunct to access to the anterior aspect of the lumbar spine. To our knowledge, there is no art suggesting cavity creation techniques or technologies for the posterior aspect to the spine such as we have described.

SUMMARY OF THE INVENTION

A novel postero-lateral, inter-muscular approach has been developed to access this commonly pathologic occiput-thoracic cervical region, more preferably C2-T1. See FIG. 11. While the description that follows specifically involves the cervical spine, many of the approach elements can be transferred to other spinal approaches.

A novel triangular surgical approach window is now described, located through the confluence of three prominent cervical muscles. Now referring to FIGS. 9A-9C, the triangle is described by;
a) the anterior superior border of the trapezius muscle;
b) the anterior inferior border of the splenius capitus muscle, and
c) the posterior superior border of the levator scapulae muscle.

Palpitation of the trapezius and the triangle is possible and blunt dissection can lead directly to the spine. No major superficial or intermediate muscle attachments or fibers are affected, and the approach follows a natural intermuscular and internervous plane to the lateral mass. The elevation of the splenius and trapezius dorsally creates and opens a potential space for deep spine access. The spinal accessory nerve is safe anteriorlly and laterally. The deep cervical artery branches are ligated with a bipolar instrument in a conventional manner, and the vertebral artery is safe anterior to the approach, protected in the foramen tranversarium. All major nerve roots are protected anteriorly in the Scalene complex. The dorsal Rami are only affected at the exposed levels similar to a posterior approach. The deep muscular layers multifide rotatores are dissected as needed for boney exposure. The natural intermuscular plane extends from C2 to T1 but can be extended even further. Unilateral foraminal root compression and central canal stenosis can be addressed with a unilateral approach, e.g., unilateral laminectomy or modified unilateral laminectomy allowing partial removal or thinning of the lamina under the spinous process. Additionally, this surgical approach lends itself to kyphotic deformities where removing the interspinous ligament and lagamentum flavums allows for restoration of lordosis and fusion of the facet and spinous processes. Laminoplasty can be easily accessed with the bilateral approach. Reconstruction options would include spinous process, posterior or lateral aspect of the lateral mass, facet or pedicle fixation. The facet complex can be viewed laterally, permitting unique access for facet decompressions, fusion, reconstruction and instrumentation. This exposure avoids all the major muscle dissection of the traditional midline approach, and for MIS considerations it allows for a contiguous surgical field unlike the current application of multiple tubes/ports. Unlike current MIS tube inset techniques, this approach spares the trapezius, spenius, levator, spinalis, and most of semispinalis capitis.

Accessing the cervical spine through this sub-splenius window also enables a new type of retractor for the support of the internal working chamber during surgery. A tent can be made by dorsally elevating the muscle fibers on the roof of the windowed opening. A lighted button is disclosed as the preferred device for making this tent, but other types of retractors can be used. New access instruments are provided for clearing and dissecting this space such as a reverse dog-bone Cobb and modular angled instruments.

The sub-splenius access also leads to new implant designs that are lateral specific or unilateral.

DESCRIPTION OF THE FIGURES

FIGS. 14-33 disclose an apparatus of the present invention involved in making a working cavity.

DETAILED DESCRIPTION OF THE INVENTION

Figure 1:
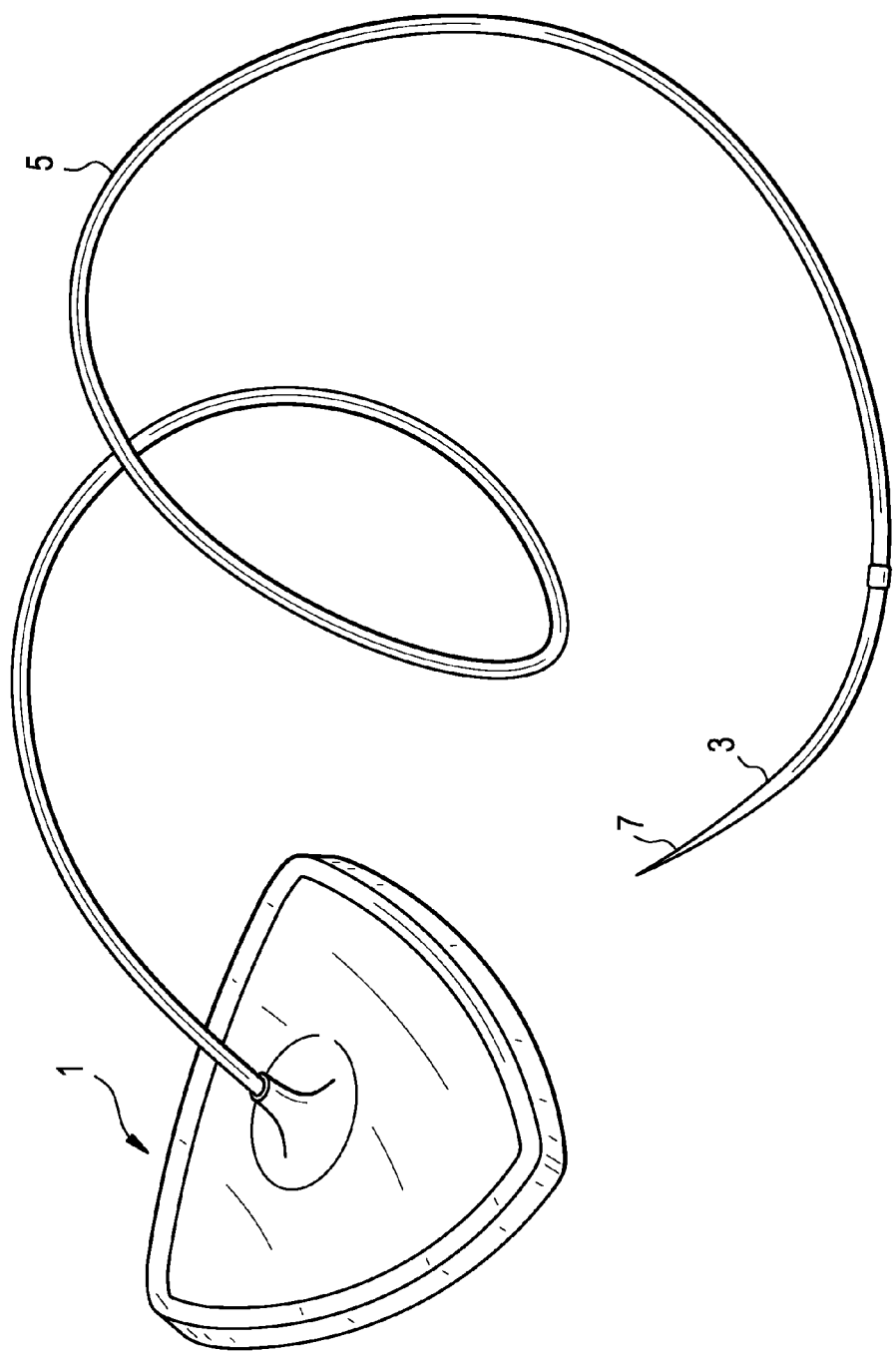
FIG. 1 discloses a retraction instrument of the present invention.
Figure 2:
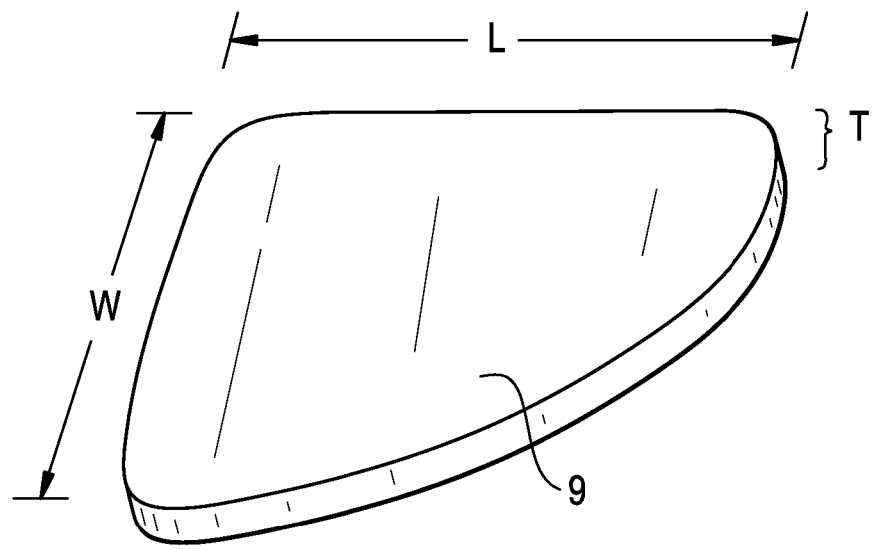
FIG. 2 discloses a retractor component of the present invention.

In one embodiment of the present invention, there is provided a surgical procedure comprising the steps of:
a) moving (preferably by lifting) the splenius capitis and trapezius muscles dorsally to create a window for deep spine access, wherein the window is defined by:
  i) an anterior superior border of the trapezius muscle;
  ii) an anterior inferior border of the splenius capitis muscle, and
  iii) a posterior superior border of the levator scapulae muscle,
b) passing a device through the window, and
c) manipulating the spine with the device.

This procedure provides the surgeon with a minimally invasive method of accessing the cervical spine via a posteriorlateral corridor that produces very little trauma because it takes novel advantage of a tissue plane between these muscles unilateral or bilateral. Accordingly, the superficial and intermediate layers of the cervical spine are completely avoided while the deep layers of the cervical spine bear only minimal disruption.

Because the above-mentioned window is adjacent the cervical spine, in some embodiments, manipulation of the spine is carried out between the second cervical and first thoracic vertebra, possibly T2.

In some embodiment, the spinal manipulation is carried out with an instrument such as a retractor. The retractor can be used to increase the access window made by moving the splenius capitis and trapezius muscles dorsally.

In some preferred embodiments, the retractor comprises a plate connected to a needle by a suture. Once this retractor has been passed into the window, the needle is passed outward through the trapezius and splenius muscle and through the skin of the patient. The needle is then pulled away from the skin to make the suture taut and thereby retract the skin of the patient away from a selected tissue of the patient and create an operative space therebetween.

In other embodiments, the device that passes through the window can be an implant. In some embodiments, the implant is selected from the group consisting of a screw, a cervical plate, a fusion cage and a motion disc rod, facet or lateral mass clamp.

In some embodiments, the procedure further comprises the step of removing a flavum selected from the group consisting of the interspinous flavum and the ligamentum flavum. Removing a flavum allows for access to the spinal canal, and decompression or correcting lordosis.

In some embodiments, the procedure further comprises the step of manipulating a facet joint complex through the window. Common procedures involving the facet joint that can be carried out through this procedure include arthrodesis partial distraction, facetectomy, reduction of dislocation, transfacet fixation, and tumor removal.

In some embodiments, the step of moving the targeted muscles comprises elevating the muscles with a balloon, table-based retractor.

Due to the novel posterolateral angle of approach provided by the present invention, the surgeon may perform the tissue plane dissection from a sitting position. Thereafter, the surgeon may be able to carry out subsequent steps, such as manipulating the spine, from the same sitting position.

In some embodiments, the tissue plane dissection step comprises the step of releasing a deep fascia between the splenius and levator scapulae muscles. This may be accomplished by digital dissection, scissors, and harmonic tools.

In some embodiments, the tissue plane dissection step comprises the step of releasing insertions of multifidi and some portion of semispinalis from the dorsal lateral mass, laminae and spinous process bases, proceeding from lateral to medial. This may be accomplished by Cobb elavator, harmonic or other energy tool such as a bovie. In some embodiments thereof, the released multifidus, along with the splenius, are lifted upwards dorsally to maintain the operative space. This dorsal upward lifting of the multifidus may be carried out by a retractor and under illumination from a light inside the patient.

Typically, the splenius capitis and trapezius muscles are accessed posterolaterally.

In some embodiments, there is provided a surgical procedure comprising the steps of:
a) dissecting the inter-muscular plane anterior to the splenius muscle to create a window, and
b) passing a device through the window.

In some embodiments, there is provided a surgical procedure comprising the steps sequential of:
a) dissecting a sub-splenius capitis/supra-levator scapulae tissue plane to create a window,
b) passing a device through the window,
c) manipulating the spine with the device, and
d) retracting one of the splenius captious and the levator scapulae to create an expanded window which forms the opening of a cave.

Preferably, the step of retracting is performed with a plate having an outer surface, wherein the outer surface bears against one of the splenius captious and the levator scapulae. Also preferably, the step of retracting is performed by pulling the plate via the needle and suture method discussed above in one or multiple vectors.

In some embodiments, this procedure further comprises the step of irradiating the window with light from a light source in order to improve the visibility of the surgeon in the deep spine region. Preferably, the light source can be located in the window to provide a high level of brightness upon the spinal area. In some embodiments, the light source is attached to the retraction plate and may also include camera tracking devices.

In some embodiments, there is provided a surgical procedure comprising the sequential steps of:
a) passing a retraction instrument inward through an incision in the skin of the patient to a location adjacent a selected tissue, wherein the retraction instrument comprises a plate connected to a needle by a suture,
b) passing the needle outward through the skin of the patient;
c) pulling the needle away from the skin to tension the suture and thereby retract the skin of the patient away from the selected tissue.

In some embodiments, there is provided a surgical procedure comprising the steps of:
a) dissecting an inter-tissue plane defined by a first tissue and a second tissue to create a window,
b) inserting a retractor into the window,
c) pulling the retractor in the direction of the first tissue Preferably, the step of pulling retracts only the first tissue and creates an expanded window. The present inventors have recognized that both sides of the window need not be retracted—that assymetrically retracting the window will be sufficient and reduce tissue trauma.

Preferably, the first and second tissues are muscles, such as the splenius capitis and levator scapulae muscles. These are the muscles that define the initial approach window.

In some embodiments, the step of pulling causes the outer surface of the plate to bear against the first tissue. This differs from the conventional means of retraction in which the tissue are pushed instead of pulled. In some embodiments, the step of pulling is accomplished by magnetic attraction. In others, the step of pulling is accomplished by pulling a ligament attached to the retractor. In still others, the step of pulling is accomplished by suction. After this retraction, the procedure typically further comprises the step of:manipulating the spine of the patient through the window.

In its broadest sense, and now referring to FIG. 1, the preferred medical retraction instrument of the present invention comprises a retractor 1 connected to a needle 3 by a suture 5.

In some embodiments, the needle has a distal end portion 7 that is curved. This curve advantageously provides ease of insertion point and a dorsalward direction. In some embodiments, substantially the entire needle is curved.

In preferred embodiments, the retractor is in the form of a plate 9 and has a width W, a length L and a thickness T, wherein the thickness is substantially less than each of the width and length. Providing a plate-like geometry to the refractor allows it to accomplish its purpose of refracting one tissue away from another while at the same time not taking up unnecessary space.

Because the location of the window is deep within the spine areas, it would be helpful to light this area so that the surgeon can have improved visibility. Therefore, in some embodiments, the surgical instrument passing through the window comprises a light with or without camera.

Figure 3:
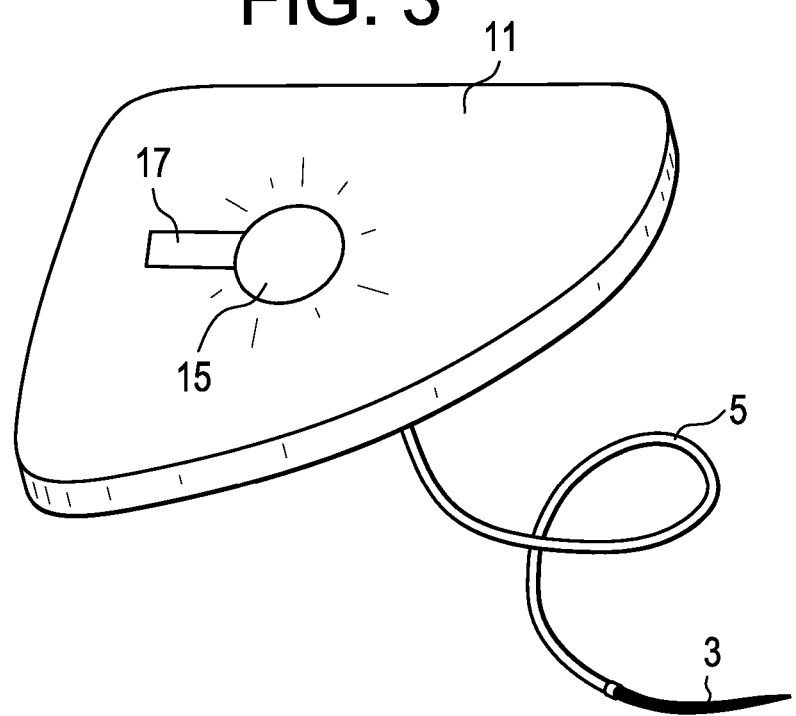
FIG. 3 discloses a retraction instrument of the present invention having a light source and battery.
Figure 4:
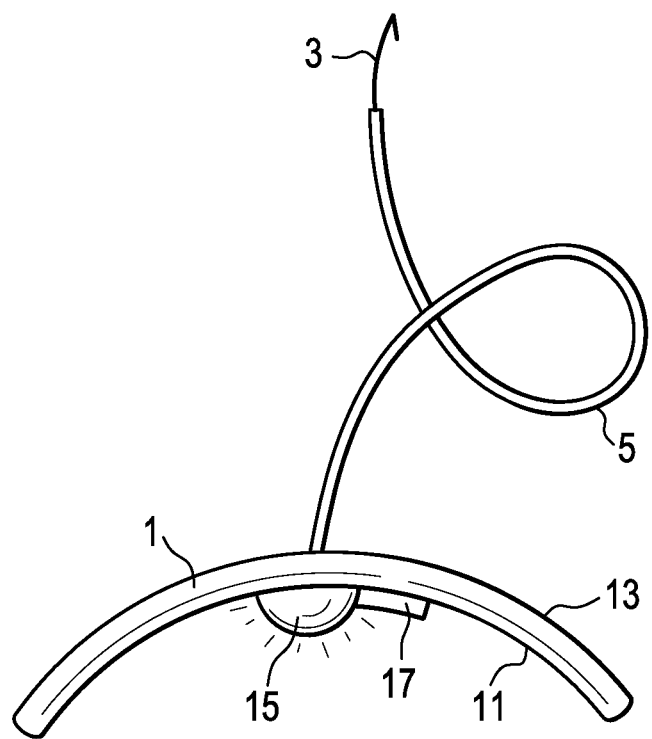
FIG. 4 discloses a retraction instrument of the present invention having a convex outer surface and a concave inner surface.

In some embodiments, and now referring to FIGS. 3 and 4, the retractor has an inner surface 11 and a convex outer surface 13, wherein the suture 5 extends from the outer surface and wherein the instrument further comprises a light source 15 connected to the inner surface. The provision of the light source on the inner surface allows the light to shine upon the spinal region.

In some embodiments, the inner surface 11 of the retractor plate is made of a reflective surface in order to better disperse the light emitted by the light source upon the window.

In some embodiments, the light source comprises an LED. Because LEDs are available in small sizes but provide high intensity light, LEDs constitute a preferred method of lighting. The light source further comprises a battery 17 connected to the LED, thereby eliminating any electrical wires from the design that may clutter up the operating theatre.

In other embodiments, however, the suture 5 may be adapted to transmit light to the inner surface of the component. This embodiment allows for the desired lighting while providing for an inexpensive instrument design.

In some preferred embodiments, the outer surface 13 is convex. This convexity allows the retractor to form a tent of the window border, thereby increasing surgeon visibility into the spinal area.

Figure 5:
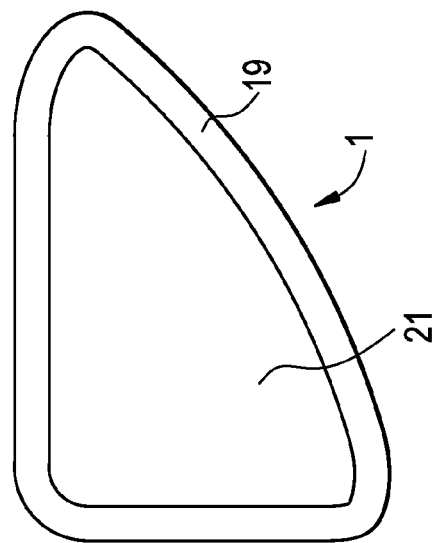
FIG. 5 discloses a retractor component of the present invention having a flexible outer rim.
Figure 6A:
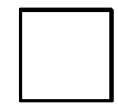
FIGS. 6a-6f disclose retractor components of various shapes.
Figure 6B:
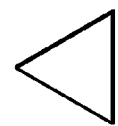
Figure 6C:
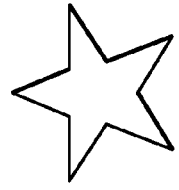
Figure 6D:
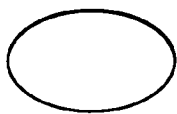
Figure 6E:
Figure 6F:
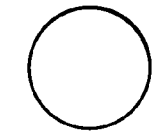

In some embodiments, and now referring to FIG. 5, the retractor has an outer rim 19 and an interior region 21, wherein the outer rim comprises a flexible material. The flexible material allows more physiologic edge loading of muscle tissue.

In some embodiments, and now referring to FIG. 6a-6f, the width and length of the retractor define an area selected from the group consisting of a substantially circular area; a substantially oval area; a star-shaped area; a substantially triangular area; a substantially rectangular area and a kidney bean area. The oval area is a preferred embodiment because it better fits the elongated opening typically made by the incision. A kidney bean shape may be used to clear the spinus process.

Typically, the retractor defines an area of between about 4 cm² to about 16 cm².

Figure 7:
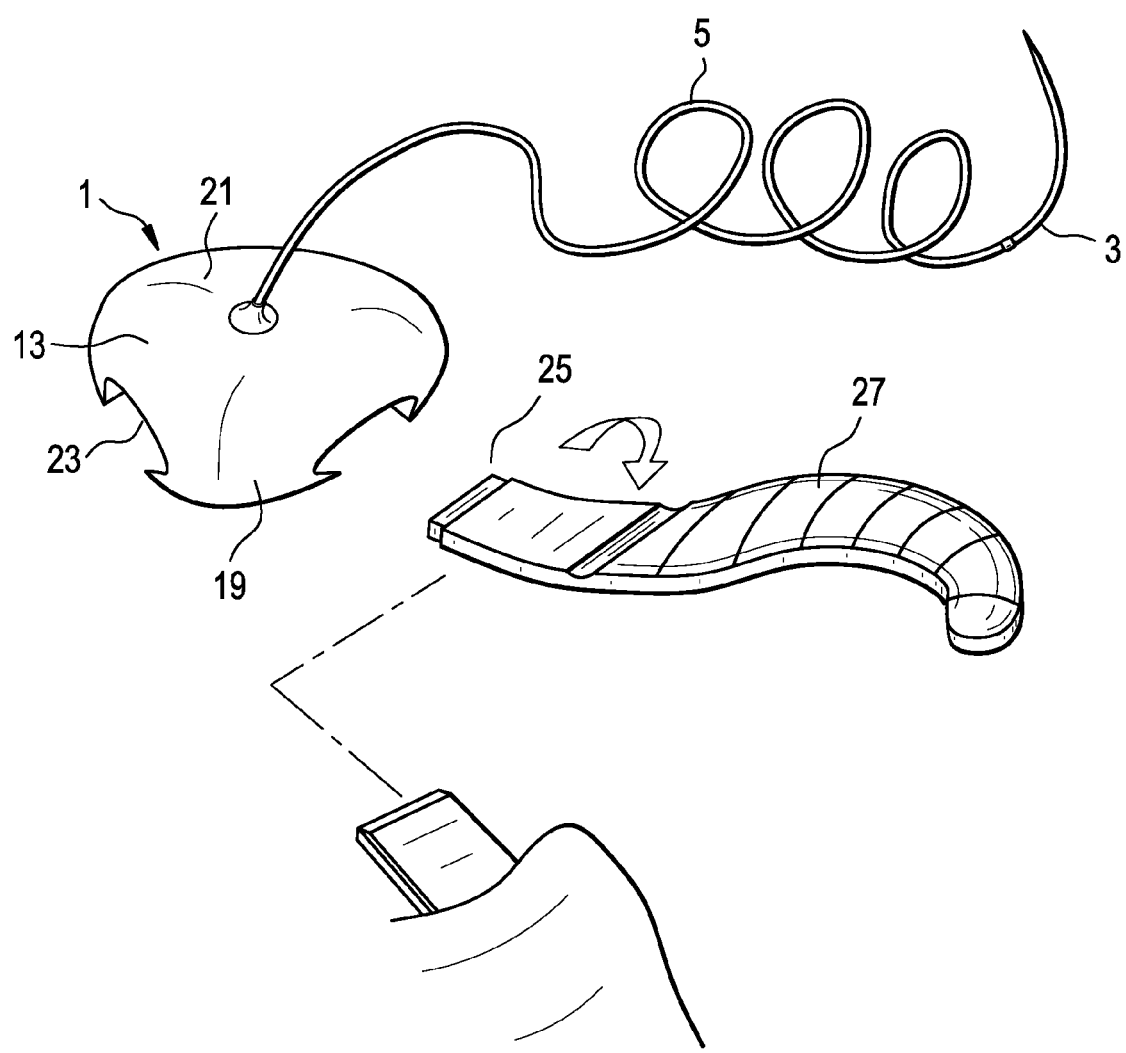
FIGS. 7, 8a and 8b disclose retraction instruments in which a wing is mated to the retractor.

In some embodiments, and now referring to FIG. 7, the retractor has an outer rim and an interior, wherein the outer rim comprises a first mating feature 23. This mating feature may be connected to a second mating feature 25 on a second component 27, such as a wing. The wing or extension provides for extra retraction area with a minimum of added bulk and ability to extend or reduce field of retraction without repositioning the suture.

In some embodiments, the retraction plate comprises a polymer. If the plate is made substantially from a polymer, its cost may be so insubstantial that it may be deemed a one-use disposable.

Figure 8A:
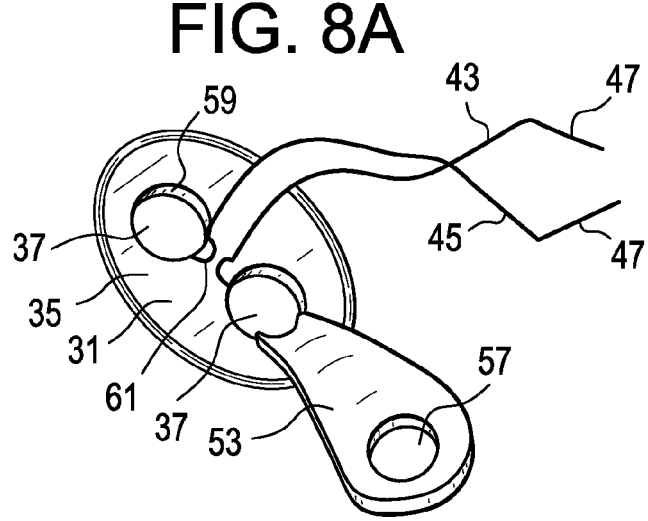
Figure 8B:
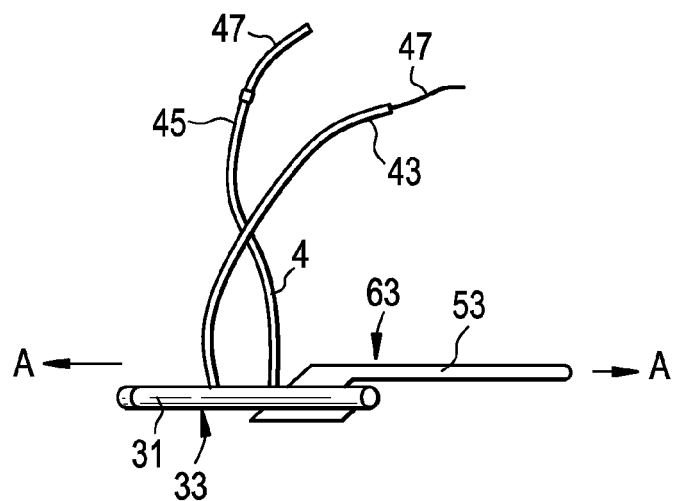
Figure 8C:
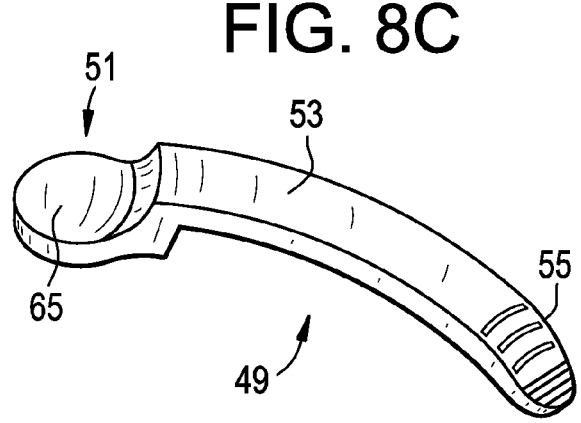
FIG. 8c discloses a wing of the retraction instrument.

In some preferred embodiments, and now referring to FIGS. 8a-8c, there is provided a medical retraction instrument comprising:
a) a plate 31 having an inner surface 33 and outer surface 35 and a pair of throughholes 37,
b) a suture 41 having first 43 and second 45 ends,
c) first and second needles 47,
d) an elongated wing 49 having a distal head 51, a shaft 53 and a proximal end portion 55,
wherein the suture passes through the first throughhole in a first direction and through the second through is an opposite direction,
wherein the first needle is connected to the first end of the suture,
wherein the second needle is connected to the second end of the suture, and
wherein the distal head of the elongated wing is passed through the first throughhole.

In some embodiments, the distal head of the elongated wing contacts the inner surface of the plate. This allows the head to swivel to adjustable and fixed angles.

In some embodiments, the proximal end portion of the elongated wing has a throughhole 57. This throughole can be used to add further wings to supporting sutures.

In some embodiments, the shaft widens from the distal head to the proximal end portion. The widening of the shaft allows for broader muscle retraction.

In some embodiments, each throughhole of the plate defines an inner rim 59 of the plate, wherein each inner rim has a recess 61. Preferably, the recesses of the inner rims oppose each other, thereby providing the elongated wings with an easy securement from either left or right (superior/inferior) directions. In some embodiments, there are multiple recesses or teeth with matching features on the wings that provide an angular adjustment and securement of the elongated wings.

In some embodiments, the shaft of the elongated wing extends from the outer surface of the plate. Because it extends from the outer surface of the plate, the wing provides an extended level of retraction in the directions needed as the surgery progresses from level to level.

In some embodiments, the shaft of the elongated wing defines a longitudinal axis A and the distal head is off-axis. The off-axis nature of the distal head provides a flip in connection that keeps the tissue-facing portion in line with the originally placed button.

In some embodiments, the shaft has an outer surface 63 and the distal head has an outer surface 65, and the outer surface of the shaft is substantially parallel to the outer surface of the distal head. There is advantage in this condition in that the edges of the field are symmetrically posted when needed.

In some embodiments, the first throughhole has a diameter, wherein the shaft of the elongated wing defines a longitudinal axis A, and the distal head of the elongated wing has a length $L_H$ in the direction of the longitudinal axis, and wherein the length of the distal head is greater than the diameter of the first throughhole. When the length of the distal head is greater than the diameter of the first throughhole, the flip in connection is not permitted to pass back through the through-hole as long as the loads on the wing are in the direction away from the tissue.

In some embodiments, the distal head has an outer surface 65, and the outer surface of the distal head of the elongated wing is substantially parallel to the inner surface of the plate. In this condition, the tissue-facing portion stays in line with the originally-placed button. This continues if additional wings are attached in chain-like fashion to the wing recesses 57.

When the proximal end portion 55 of the elongated wing component is curved, the wing advantageously traverses an offset to retract tissue that is not directly in line with the originally placed button.

Figure 9:
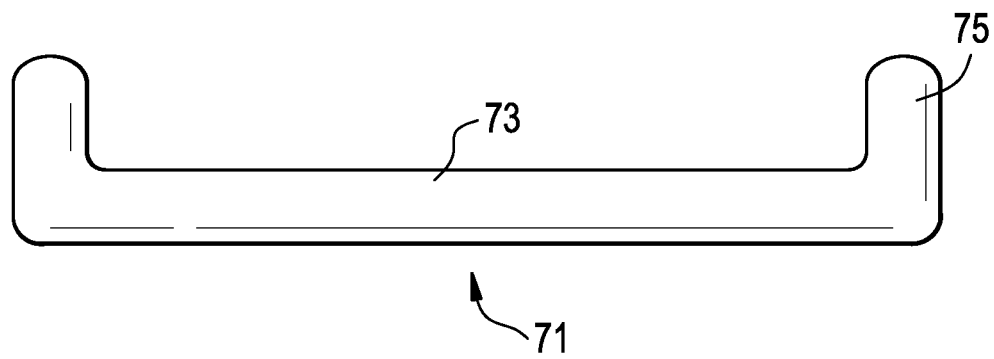
FIG. 9 discloses a plate having an outer rim and an interior region 73, wherein the interior region of the plate defines a plane, wherein the outer rim of the plate extends out of the plane of the plate.
Figure 9A:
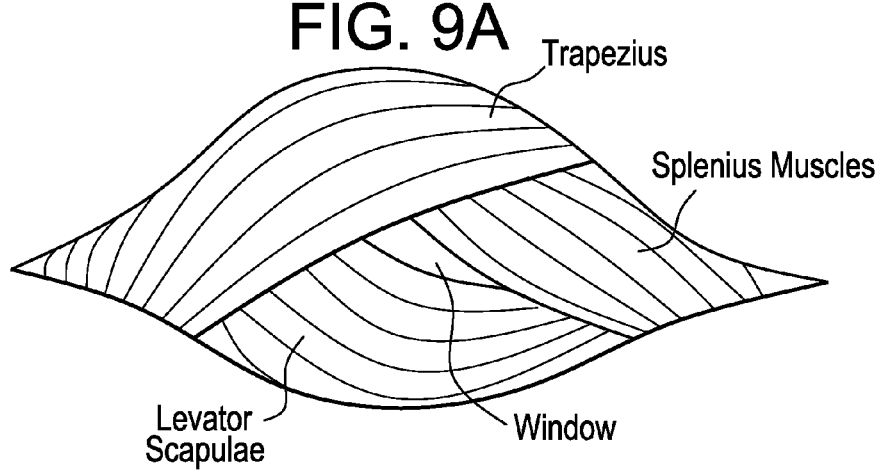
FIGS. 9A-9C disclose views of the access region of the present invention
Figure 9B:
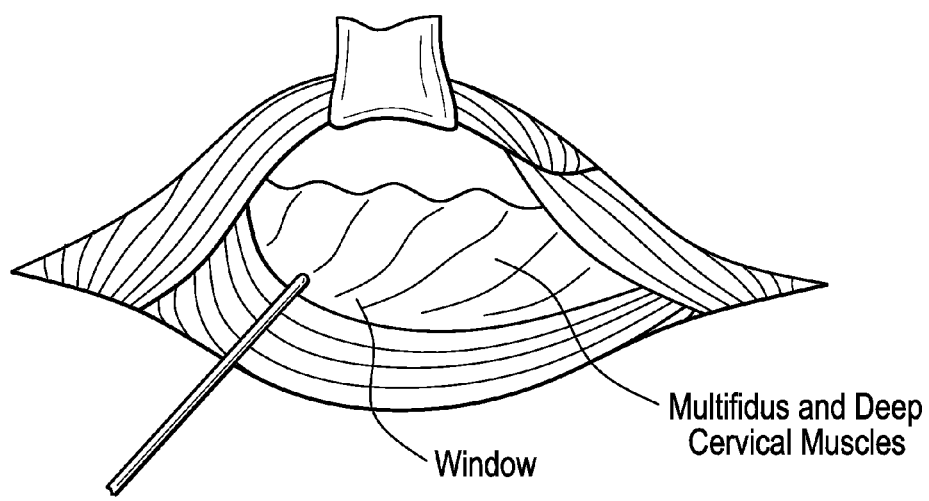
Figure 9C:
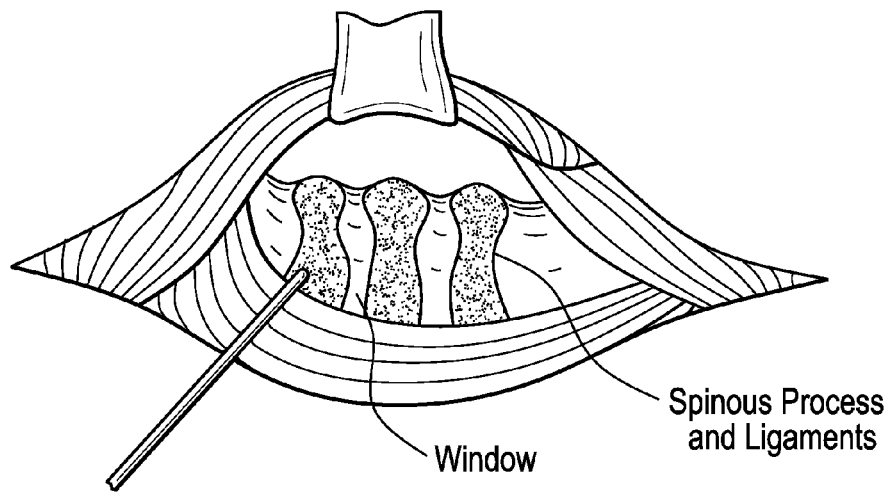
Figure 10:
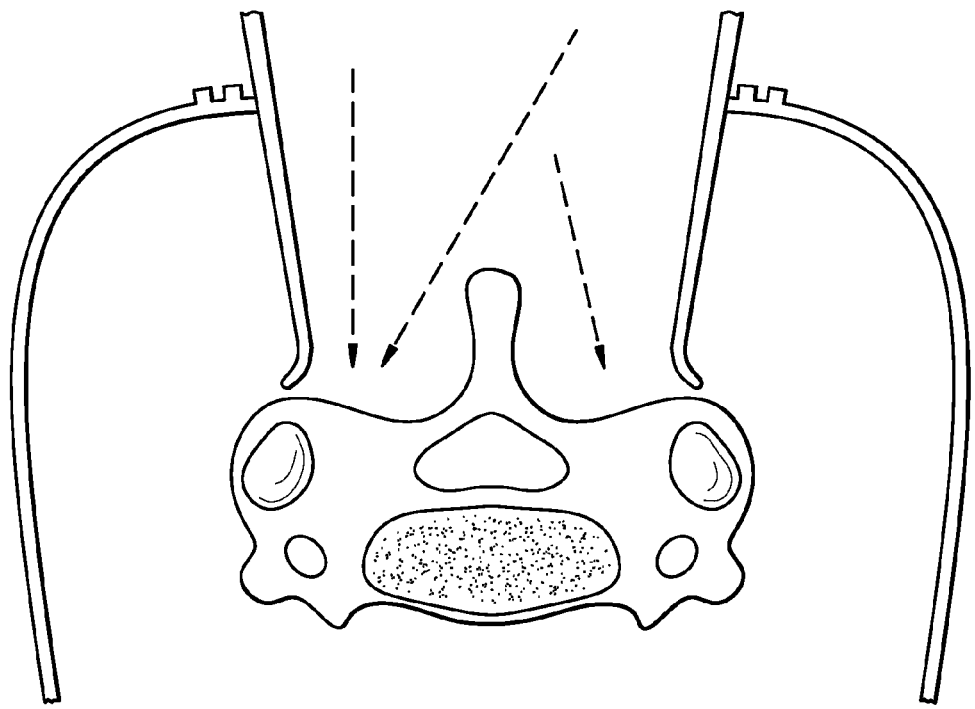
FIG. 10 discloses the trajectories of conventional approaches to the cervical spine.
Figure 11:
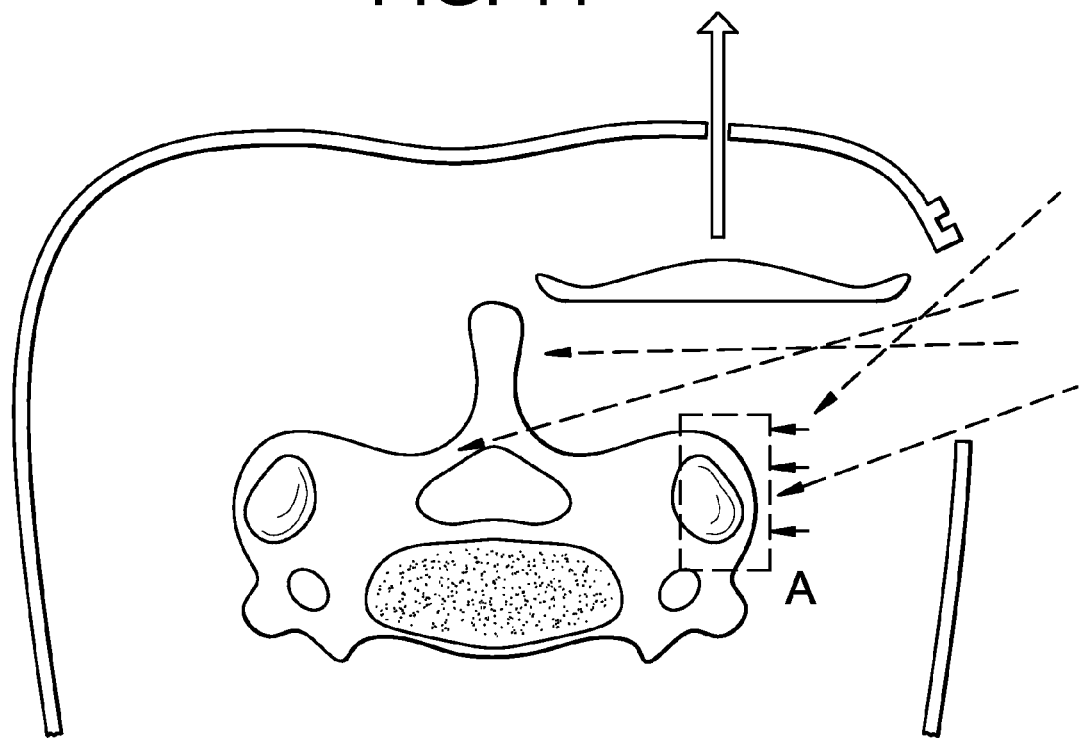
FIG. 11 discloses the trajectories of approaches to the cervical spine providing by the present invention.

In some embodiments and now referring to FIG. 9, the plate 71 has an outer rim 75 and an interior region 73, wherein the interior region of the plate defines a plane, wherein the outer rim of the plate extends out of the plane of the plate. When the outer rim of the plate extends out of the plane of the plate, this advantageously fixates the plate in the tissue and provides for distributing the loads on the tissue. A transition zone at the extents of the plate can be used to soften or tighten the grip on the tissue.

Also in accordance with the present invention, there is provided a magnetic comprising:
a) a ferromagnetic plate having an inner surface and an outer surface,
b) a light source attached to the inner surface of the plate, This magnetic retractor can be placed within the window and then coupled across the patient's skin with a second magnet. The second magnet can then be pulled to lift the skin and thereby create an expanded window. Preferably, the outer surface of the plate comprises a ferromagnetic material.

In some embodiments, the ferromagnetic material is either iron or a rare earth. Avoids requirement for passage of needle while allowing quick connect—disconnect for adjustment.

In some embodiments, the method steps of the present invention may be undertaken manually by a surgeon. In other embodiments, these method steps are undertaken robotically. In others, the method steps are undertaken by a mixture of manual steps and robotic steps.

The methods of the present invention are intended to be carried out broadly in the occiput-thoracic cervical region. Preferably The methods of the present invention are intended to be carried out broadly in the C2-T1. T2 is potentially accessible via the upper thoracic region. Above about C2, more injury would be contemplated.

In some embodiments, a lapascope may be used to provide the positive pressure and the insufflation necessary to retract tissue.

Further, it is believed that the unilateral laminectomy with spinous process fixation that can be achieved through this approach has a comparable biomechanical stability to unilateral lateral mass screws and unilateral pedicle screw fixation. It also approaches the stability provided by bilateral lateral mass screw fixation, which is considered to be the standard of care today.

(FIGS. 12)

Now referring to FIGS. 12a-12m, there are provided a number of different embodiments involving the retractor of the present invention with additional performance-enhancing features attached thereto.

Figure 12A:
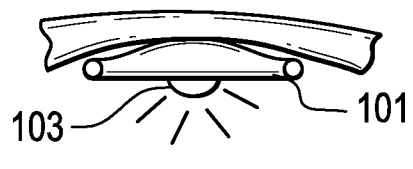
FIGS. 12a-12m disclose a number of different embodiments involving the retractor of the present invention with additional performance-enhancing features attached thereto.
Figure 12B:
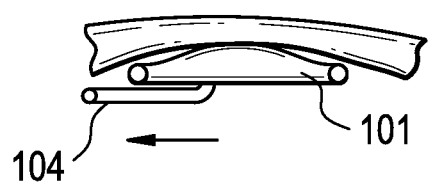
Figure 12C:
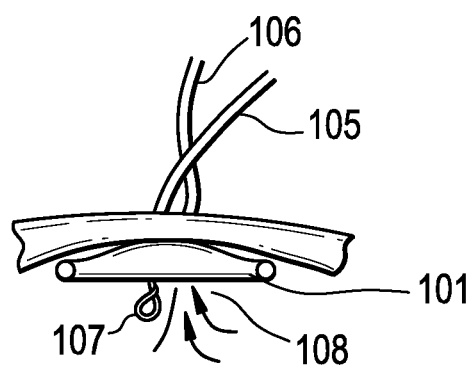
Figure 12D:
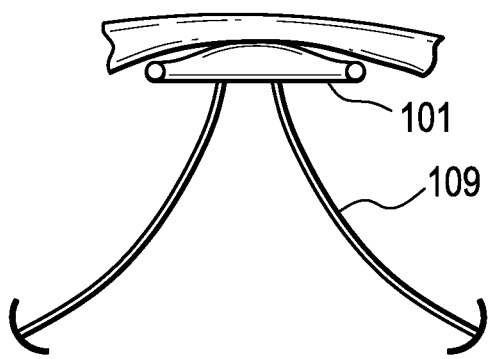
Figure 12E:
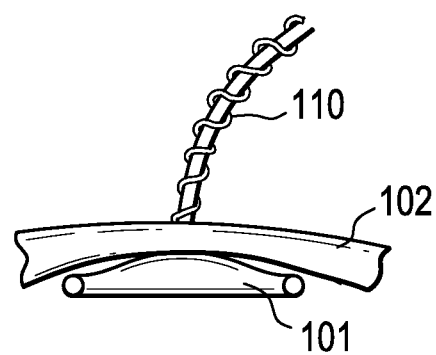
Figure 12F:
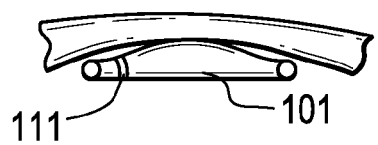
Figure 12G:
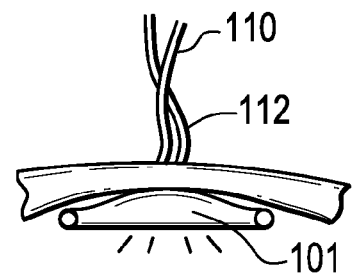
Figure 12H:
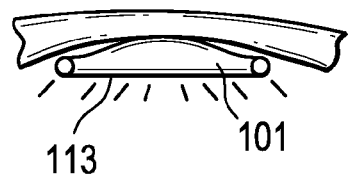
Figure 12I:
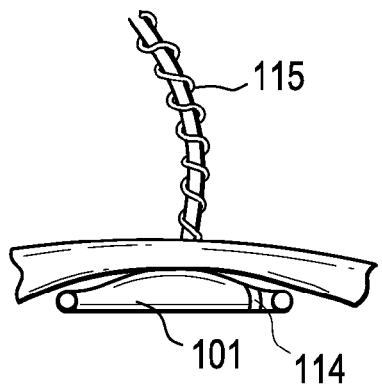
Figure 12J:
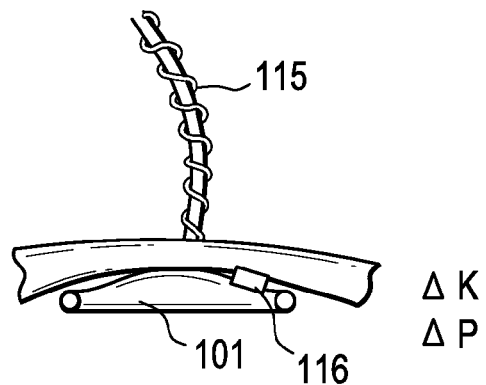
Figure 12K:
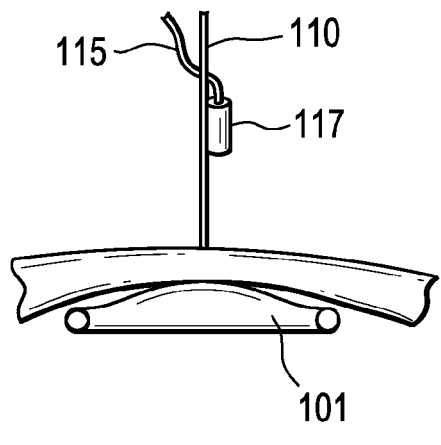
Figure 12L:
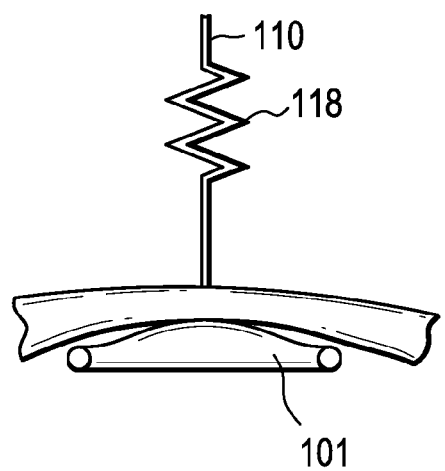
Figure 12M:
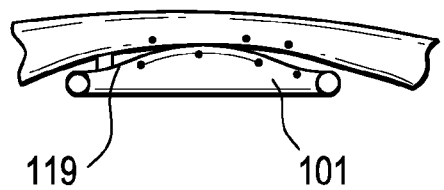

In FIG. 12a, the retractor 101 is provided with a light emitting device 103. This diode can increase the surgeon's visibility of the working environment with the cavity. In FIG. 12b, the retractor 101 is provided with a telescopic extension 104 that slides outwards to extend the reach of the retractor, thereby widening the footprint of the cavity. In FIG. 12c, the refractor 101 is provided with a number of irrigation and suction options, including an irrigation tube 105 having an irrigation port 107, and a suction tube 106 having a suction port 108. These options allow the surgeon to use irrigation fluid within the cavity, thereby assisting in cleaning the cavity of loose tissue. In FIG. 12d, the retractor 101 is provided with supporting legs 109 that hold open the cavity made by the retractor. This enhances or stabilizes the volume of the cavity. In FIG. 12e, the retractor 101 is connected to a suture 110 that passes through the patient's skin 102. When the suture is tensioned from outside the patient, it enhances or stabilizes the volume of the cavity. In FIG. 12f, the retractor 101 is radiolucent and is provided with a radiopaque marker 111 that allows the retractor to be located on an x-ray. In FIG. 12g, the retractor 101 is provided with both a suture 110 and a fiberoptic cable 112. Light emitted through the fiberoptic cable can increase the surgeon's visibility of the working environment with the cavity. In FIG. 12h, the retractor 101 is provided with a light-emitting coating 113, such as a phosphorescent (glow-in-the dark) coating. In FIG. 12i, the retractor 101 is provided with a neuromonitoring feature 114 (such as an electrode) connected to an electrical cable 115. The electrode can help the surgeon detect nervous tissue in the vicinity of the cavity. In FIG. 12j, the retractor 101 is provided with temperature/pressure controls, such as sensor 116 (which can be either a temperature or pressure sensor) connected to an electrical cable 115. A pressure sensor can help the surgeon determine whether the retractor is imparting an unsuitably high pressure or stress upon the tissue surrounding the cavity. In FIG. 12k, the retractor 101 is provided with a strain gauge sensor 117 for measuring tension, wherein the sensor is connected to a suture 110 and an electrical cable 115. In FIG. 12l, the retractor 101 is provided with spring scale 118 for measuring force, wherein the spring scale is connected to a suture 110. In FIG. 12m, the retractor 101 is provided with an anti-infective coating 119. This coating helps prevent bacteria from moving from the retractor to the patient's tissue, thereby preventing infections.

Now referring to FIGS. 13a-13m, there are provided a number of different embodiments involving the retractor of the present invention with additional support features attached thereto.

Figure 13A:
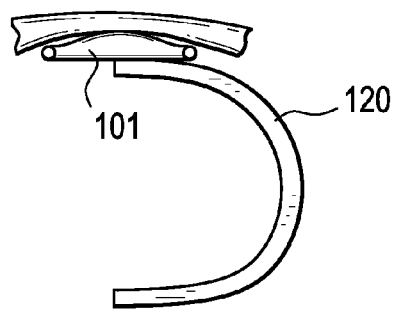
FIGS. 13a-13p disclose a number of different embodiments involving the retractor of the present invention with additional support features attached thereto.
Figure 13B:
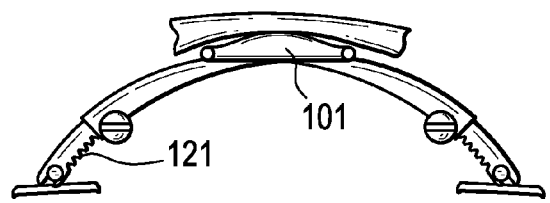
Figure 13C:
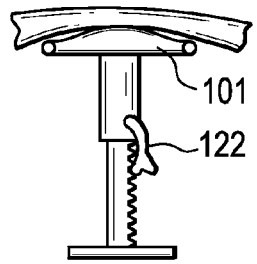
Figure 13D:
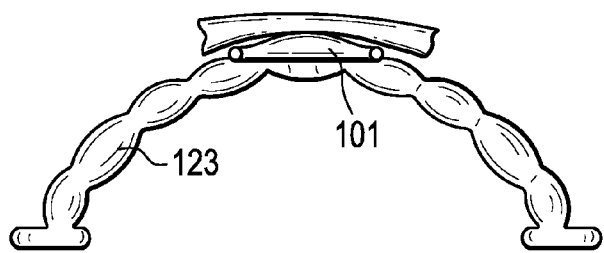
Figure 13E:
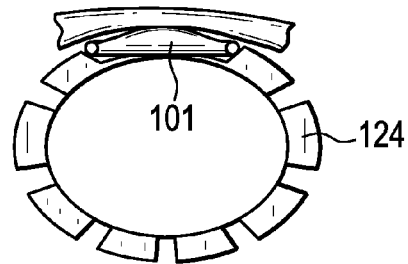
Figure 13F:
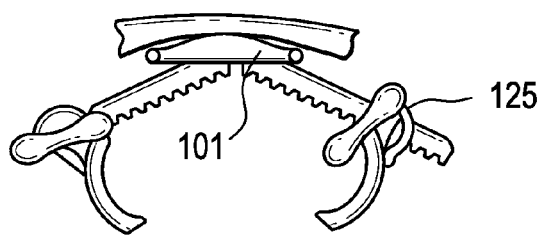
Figure 13G:
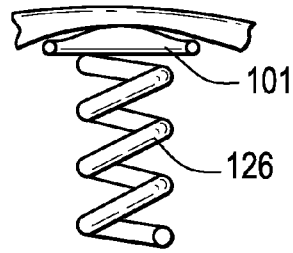
Figure 13H:
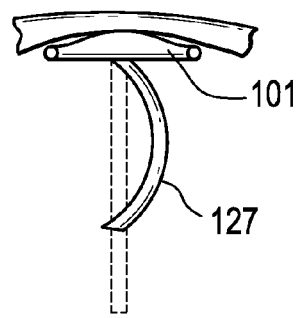
Figure 13I:
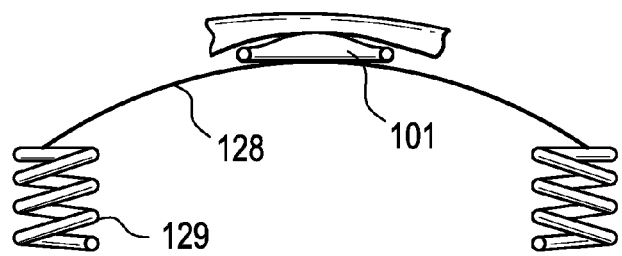
Figure 13J:
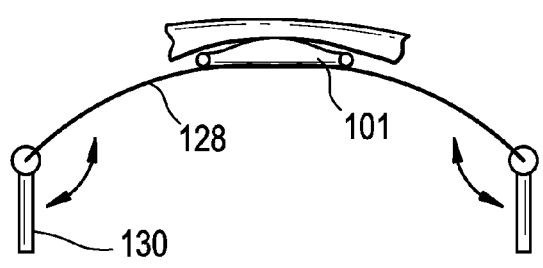
Figure 13K:
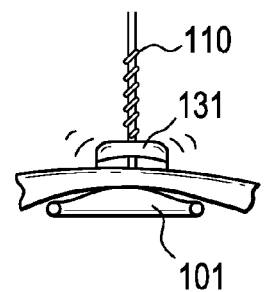
Figure 13L:
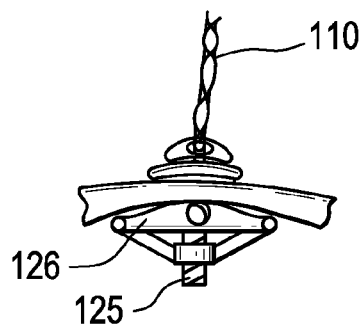
Figure 13M:
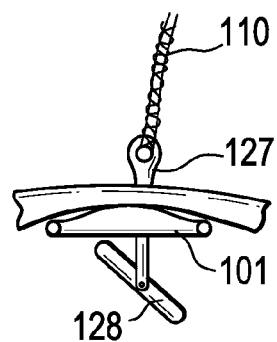
Figure 13N:
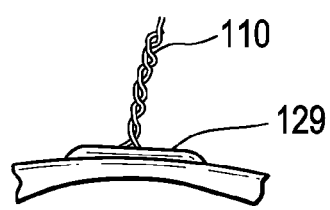
Figure 13O:
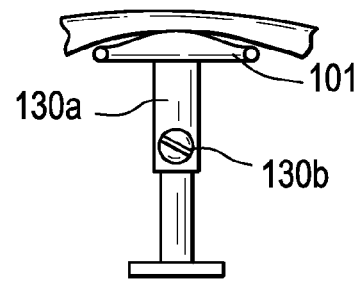
Figure 13P:
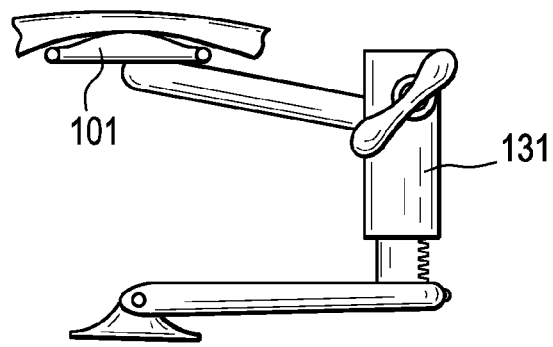
Figure 33:
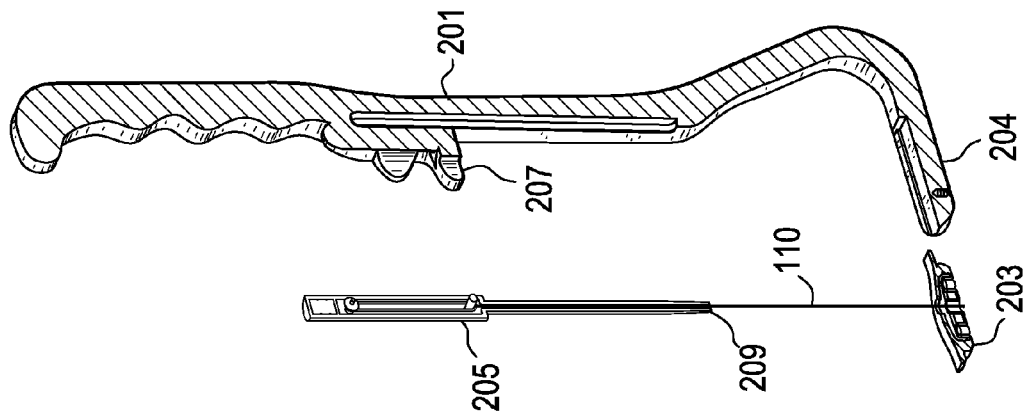

In FIG. 13a, the retractor 101 is provided with support from inside the cavity by a C-shaped clip 120. In FIG. 13b, the retractor 101 is provided with support from inside the cavity by a gear/rack type telescopic arch 121. In FIG. 13c, the refractor 101 is provided with support from inside the cavity by a jack-type telescopic column 122. In FIG. 13d, the retractor 101 is provided with support from inside the cavity by an inflatable arch 123 (providing tent-like support). In FIG. 13e, the retractor 101 is provided with support from inside the cavity by a circumferential spring sheet 124. In FIG. 13f, the retractor 101 is provided with support from inside the cavity by a dual rack retractor blade assembly 125. In FIG. 13g, the retractor 101 is provided with support from inside the cavity coil spring 126. In FIG. 13h, the retractor 101 is provided with support from inside the cavity by a memory metal-based spring 127 (made of, for example, nitinol). In FIG. 13i, the retractor 101 is provided with support from inside the cavity by coil springs 129 connected by a beam 128. In FIG. 13j, the refractor 101 is provided with support from inside the cavity by folding legs 130 connected by a beam 128. In FIG. 13j, the metallic retractor 101 holds the cavity open via attraction to a magnet 131 located outside the patient. In FIG. 13l, the cavity is held open with tension from outside the patient (via suture 110) and with a wall type anchor having two legs disposed inside the cavity. The anchor comprises a threaded anchor portion 125 and a folding anchor linkage 126. In FIG. 13m, the cavity is held open with tension from outside the patient (via suture 110) and with a wall type anchor having a single leg disposed inside the cavity. The anchor 127 comprises a toggle leg 128. In FIG. 13n, the cavity is held open with tension from outside the patient (via suture 110) through the use of adhesive tape 129. In FIG. 13o, the retractor 101 is provided with support from inside the cavity by a telescopic tube 130a secured by a set screw 103b. The tube portions are slid apart and then held in place. In FIG. 13p, the retractor 101 is provided with support from inside the cavity by cervical refractor-type device 131.

EXAMPLE I

The patient is positioned prone, but the surgeon is comfortably sitting. This approach can be unilateral or bilateral, normally for access up to $C_2$-$T_1$. A longitudinal skin incision is based on the lateral boarder of the Trapezius, preferably in the range of 20-30 mm long and radiographically localized if needed. The superficial fascia is opened (20-85 mm or more) preferably with Metz along the lateral Trapezius boarder in the rage of (30-35 mm). The Levator scapulae is digitally identified laterally, and the deep fascia opened between the Splenius and Levator scapulae muscle. This plane can be opened bluntly with finger dissection or with metz from 10 mm (up to 150 mm) as needed. The Spinal Accessory nerve is safe, resting anteriorly and laterally on the anterior boarder of Levator Scapulae, and is not retracted or involved in the approach. Blunt digital dissection is directed straight medially and quickly identifies the lateral mass and the dorso-lateral corner of the facet joint. Confirmation of desired spinal level is done under direct or assisted visualization, palpation (e.g. finger sensing) and radiographically.

Up to this point only limited unilateral fascial release has been required and no muscle origins or insertions have been disturbed. The superficial and Intermediate cervical muscular layers and ligamentous structures remain intact dorsally. The extent of release of the superficial and deep facia is governed by the number of vertebral levels to be accessed much like an anterior cervical approach. Once the anatomic level is confirmed, dissection is taken cephalad and candally only over the levels needed. A contiguous unilateral field of exposure from $C_2$ to $T_1$ can be obtained. Unlike tubular MIS approach systems, this approach provides a fully continuous surgical field at the target. The insertions of multifidi are released form/dissected off the dorsal lateral mass, laminae and spinous process bases proceeding from lateral to medial. The facet capsules can be spared or removed as indicated. The Nuchal, interspinous and supraspinous ligaments are preserved, as well as ligamentum flavum, and all major muscle groups. Once released, the multifidus, along with the splenius, semispinalis and trapezius are lifted upwards dorsally with either standard or special retractors with or without illumination port to maintain the operative space. The retraction is not a typical opposed bidirectional system, but has a single multidirectional vector which puts no pressure on anterior structures. Complete posterior boney exposure can extend unilaterally from the spinus process base medially across the lamina and facet to the lateral surface of the lateral mass. This entire dissection is all done unilaterally and many pathologies could be addressed without disturbing the contralateral tissues. If indicated, the entire spinius process and interspinious space can be accessed laterally by dissecting the spinalis. If needed, bilateral exposure can be accomplished through a matching skin incision on the other side, and the left and right surgical fields could be connected across the midline. Closure requires 1-2 sutures in the deep fascia, 2-3 sutures in the superficial fascia and a subcuticular skin closure. There is no muscle or ligamentous reattachment required. It is possible that this dissection would allow same day discharge.

No major superficial or intermediate muscle attachments are affected, and the approach follows a natural intermuscular and internervous plane to the lateral mass. The anatomic elevation of the splenius and trapezius dorsally creates and opens a natural potential space ventral to the muscles for deep spine access. The spinal accessory nerve is safe anteriorly and laterally. The small deep cervical artery branches running on the lateral lamina would be bipolared in usual fashion for posterior approach, and no significant vascular structures lie along this path between C2 and T2. If one crossed above to the C1 lamina the vertebral artery at C1 could be accessed. In this described approach to C2-T2, the vertebral artery is safe anterior to the approach, protected in the foramen transversarium. All major nerve roots are protected anteriorly in the Scalene complex, and not subject to retraction. The dorsal rami are only affected at the exposed level(s) similar to a posterior approach, although fewer levels would need to be exposed for the same pathology. Unilateral foraminal nerve root compression and central canal stenosis as well as posterior ligament ossifications can be addressed with a unilateral approach, e.g. unilateral laminectomy/facetectomy or modified unilateral laminectomy with internal laminoplasty allowing partial removal or thinning of the lamina under the spinous process centrally. Additionally, this surgical approach lends itself to kyphotic deformities were removing the interspinous and Ligamentum Flavums allows for restoration of lordosis and fusion of the facets & spinous processes. Laminoplasty can be easily accessed with the bilateral approach. Far lateral dissection anterior to the lateral mass could provide access to the post foraminal roots and plexus if needed. Reconstructive options would include spinous process, lateral mass, or pedicle fixation. The facet complex can be viewed laterally permitting unique access for facet decompression, as well as fusion, reconstructions and instrumentation if needed FIG. 14 of the disclosure shows an operative window opening O being held open by a device of the present invention during surgery. The skin has been incised to create the opening O, a chandelier-type retractor (not shown in FIG. 14) has been inserted through the opening below the tissue to be retracted, and a punch 205 with attached suture 110 is being used to lift the chandelier (and thereby the tissue) to create a working cavity.

One embodiment of the procedure of the present invention is as follows:

Following the preparation of the operative window via incision and blunt dissection, a surgeon loads the correct size chandelier-type retractor 203 onto a channel 118 in the distal portion 204 of the holder 201 as shown in FIGS. 17 and 18. The Chandelier-type retractor 203 is then inserted into the operative window opening O, as shown in FIG. 15.

As shown in FIG. 19, the punch 205 and the punch sled 207 are plunged proximally-to-distally so that the punch point 209 makes a definitive connection with the chandelier 203. This is shown in cross-section in FIGS. 25 thru 27. This connection is both mechanical and electrical.

Figure 31:
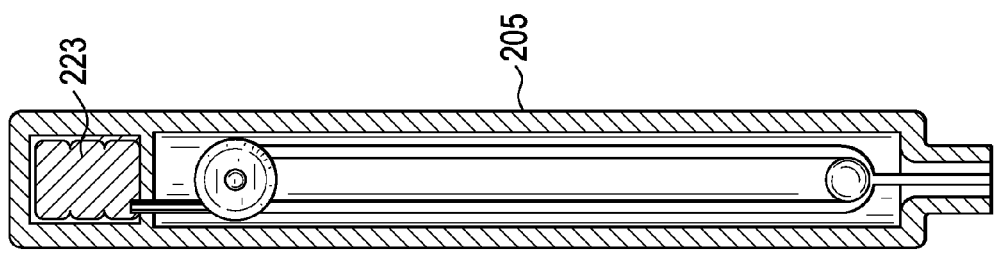

After the connection to the chandelier 203 is made, the punch 205 and punch sled 207 are pulled distally to proximally, leaving a trailing amount of the suture 110, as shown in FIG. 16 and FIG. 20. This is shown in cross-section in FIGS. 28 thru 30. The suture 110 is allowed to trail behind due to the excess suture available, pre-packed or wound within the punch 205, as shown in FIG. 31. The suture 110 reaches a limiting length so that the punch 205 can be used to tension the chandelier 203.

After the punch sled 207 has returned to its original proximal position, the punch and punch sled can be disconnected from the holder 201, and the distal portion of the holder can be removed from the window, as shown in FIG. 17. The holder can then be manipulated by an operating room attendant or it can be parked upon a frame that supports the holder at the correct vector above the operating window. The frame can be fixed to the surgical bed on a rail or post arm or can be fixed to any operating room stand, hook, or pole.

Figure 32:
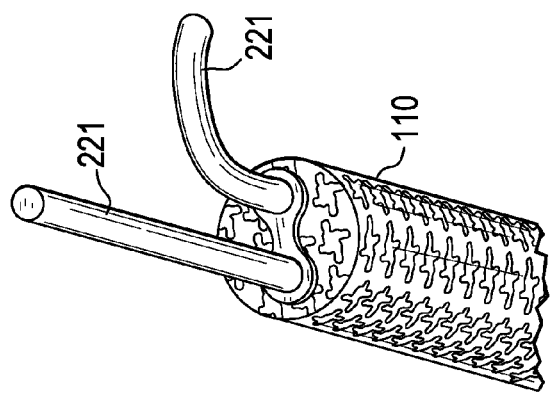

The chandelier 203 may have a light. The lighted portion of the chandelier may be actuated by battery connection. As shown in FIG. 24, the chandelier consists of a bi-polar receptacle 210 at its center with circuitry leading to LED lamps 211. The point 209 of the punch 205 has a two-conductor geometry similar to a common head phone jack as shown in FIG. 27. The plus and minus wires 221 from the batteries 223 (FIGS. 31 and 32) are incorporated into the suture 110 (FIG. 32) and connected respectively to each of the conductor poles. As the chandelier connection is made, the battery power travels through the receptacle and the chandelier lights turn on. In one preferred embodiment, the batteries are stored within the punch. However, the batteries can also be sealed within the chandelier and turned on with a switch or by removing a sterile insulating strip between the batteries. In this manner, the suture would not need to incorporate electrical wiring—it would need only support the retraction forces.

The methods of the present invention may find utility in the following surgical procedures:
1. Cervical laminectomy: used for cervical stenosis (congenital and acquired), cervical spondylotic myelopathy, multilevel spondylotic radiculopathy, ossification of the posterior longitudinal ligament (OPLL), ossification of the yellow ligament (OYL), neoplasm, and infection. MIS unilateral decompression using laminectomy and posterior cervical stabilization and fusion can be achieved using either:
   a) Pedicle screws/rods fixation
   b) Spinous process screws/rods or plate fixation
   c) Translaminar plates/screws fixation
   d) Lateral screws/rods fixation
   e) Facet screws
   f) Bilateral laminectomy/Laminoplasty 2. Single level foraminotomy for radiculopathy (including unilateral foraminotomy and unilateral facetectomy);
3. Posterior element tumor resection;
4. Brachial Plexus Surgery;
5. ORIF Cervical Fracture; and
6. Posterior Cervical Fixation (traditional lateral mass/cranio-thoracic).

The natural lordotic curvature of the cervical spine distributes the compressive load differently than in other spinal locations. The cervical spine transmits 36% of compressive loads through the anterior column, while 64% is borne through the posterior column facet joints. (Beck D McAllister, Brandon J Rebholz, Jeffery C Wang; Is posterior fusion necessary with laminectomy in the cervical spine? Surgical Neurology International Spin, E, *Surg Neurol Int* 2012, 3:225) In order to preserve stability, the surgeon needs to recognize the potential destabilizing impact of a posterior approach as laminectomy, facetectomy (medial, partial, or full) may contribute to instability/deformity. When performing cervical laminectomies, the extent of facetectomy performed over single or multiple levels helps to determine the development of instability. If it is necessary to perform multiple foraminotomies, or resect greater than 30-50% of the facet joint, it is recommend the addition of a posterior cervical fusion to avoid iatrogenic instability. (Beck D McAllister, Brandon J Rebholz, Jeffery C Wang; Is posterior fusion necessary with laminectomy in the cervical spine? Surgical Neurology International Spine, E, *Surg Neurol Int* 2012, 3:225).

Unilateral foraminal nerve root compression (radiculopathy) can be addressed with a unilateral foraminotomy and central canal stenosis and/or posterior ligament ossifications (PLL) causing myelopathy can also be addressed by a multilevel unilateral laminectomy with or without partial removal or thinning of the lamina under the spinous process centrally and stabilization with unilateral facet screw fixation, laminoplasty plates/screws, pedicle or lateral mass screw/rod fixation or even spinous process screws/rod or plate fixation.

Additionally, this surgical approach lends itself to kyphotic deformities were removing the interspinous and Ligamentum Flavums allows for restoration of lordosis and fusion of the facets and/or spinous processes and fixation using facet screws, lateral mass screws/rods or pedicle screws/rods or spinous process anchors with rods or plates. This technique also can be used to augment the stability of multilevel anterior cervical fusion.

Unilateral laminectomy and laminoplasty can be easily accessed with the bilateral approach. Far lateral dissection anterior to the lateral mass could provide access to the post foraminal roots and plexus if needed. Reconstructive options would include laminoplasty screws/plates, spinous process, lateral mass, or pedicle fixation. The facet complex can be viewed laterally permitting unique access for facet decompression, as well as fusion, reconstructions and instrumentation if needed.

Figures 34A, 34B, 34C:
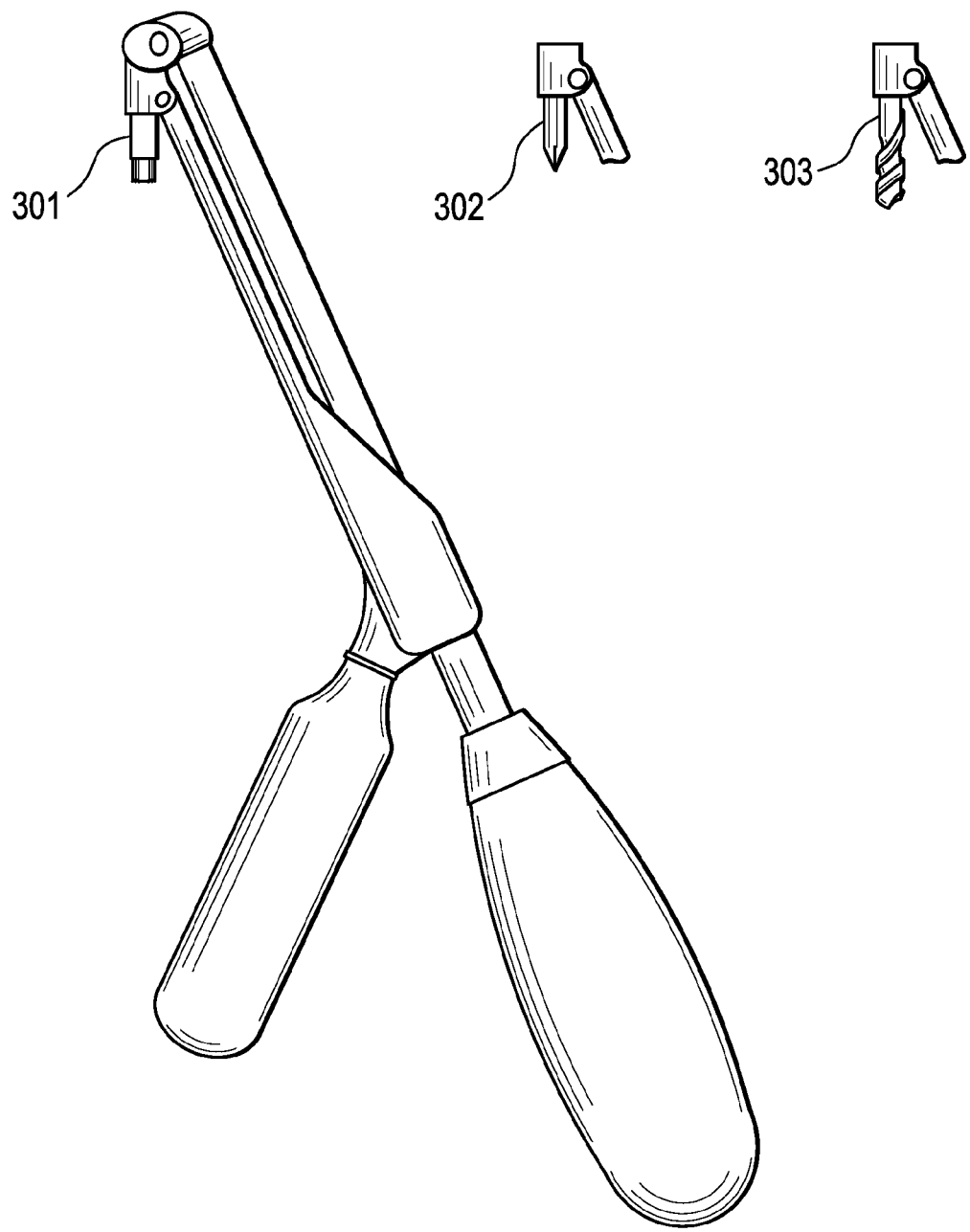
FIGS. 34a-c disclose articulating instruments that can be used in carrying out the present invention.

Some challenges associated with this approach include an unfamiliar orientation for dissection, dorsal ramus dissection, limited access to anterior floor of spinal canal, and the need for some articulated instruments. Now referring to FIGS. 34*a-c*, there are provided articulating instruments that can be used in carrying out the present invention. The working tips of these instruments can be a driver 301, an awl 302 and a drill 303.

There are numerous advantages associated with this approach. For example, this exposure avoids all major muscle dissection of the traditional posterior midline approach, and for MIS considerations it allows for a contiguous surgical field unlike the current application of multiple tubes/ports. No vital structures are presented in route, and there appear to be no catastrophic potential risks as exist with anterior approach. The approach is, relatively quick and may be carried out from a comfortable sitting position for operating team providing ergonomic improvement for the surgeon. The approach, often only be needed unilaterally to preserve function.

We claim:
1. A surgical procedure for a spine of a patient comprising:
incising the skin of the patient in the postero-lateral region of the cervical spine;
moving the splenius capitis and trapezius muscles dorsally via one of a blunt instrument and a finger to create a window for deep spine access, wherein the window is defined by:
i) an anterior superior border of the trapezius muscle;
ii) an anterior inferior border of the splenius capitis muscle, and
iii) a posterior superior border of the levator scapulae muscle;
passing a device through the window; and
manipulating at least a portion of the spine of the patient through the window;
whereby after completion of the surgical procedure in the deep spine, there is no muscle reattachment required for the trapezius muscle, the splenius capitis muscle, and the levator scapulae muscle.

2. The surgical procedure of claim 1 further comprising:
creating a large space or cavity through or inside the window.

3. The surgical procedure of claim 2 wherein the device is an implant.

4. The surgical procedure of claim 1 wherein the manipulation is carried out between the second cervical and first thoracic vertebra.

5. The surgical procedure of claim 1 wherein the device is an instrument.

6. The surgical procedure of claim 5 wherein the instrument is a retractor.

7. The surgical procedure of claim 6 wherein the instrument comprises a light.

8. The surgical procedure of claim 5 wherein the instrument comprises a plate connected to a needle by a suture.

9. The surgical procedure of claim 8 further comprising:
passing the needle through the skin of the patient.

10. The surgical procedure of claim 9 further comprising:
pulling the needle away from the skin to make the suture taut and thereby retract the skin of the patient away from a selected tissue of the patient and create an operative space there between.

11. The surgical procedure of claim 1 further comprising:
removing a flavum selected from the group consisting of the interspinous flavum and the ligamentum flavum.

12. The surgical procedure of claim 1 further comprising:
manipulating a facet joint complex through the window.

13. The surgical procedure of claim 1 wherein moving comprises elevating.

14. The surgical procedure of claim 1 wherein the surgeon is in a sitting position during the moving.

15. The surgical procedure of claim 1 wherein the moving includes releasing a deep fascia between the splenius capitis and levator scapulae muscles.

16. The surgical procedure of claim 1 wherein the moving includes releasing insertions of multifidi and lateral semispinalis from the dorsal lateral mass, laminae and spinous process bases proceeding from lateral to medial.

17. The surgical procedure of claim 16 wherein the released multifidi, along with the splenius, are lifted upwards dorsally to maintain the operative space.

18. The surgical procedure of claim 17 wherein the dorsal upward lifting of the multifidi is carried out by a retractor.

19. The surgical procedure of claim 17 wherein the dorsal upward lifting of the multifidi is carried out under illumination from a light inside the patient.

20. The surgical procedure of claim 1 wherein the splenius capitis and trapezius muscles are accessed posterolaterally.

* * * * *